US011179311B2

(12) United States Patent
Gudmundsdottir et al.

(10) Patent No.: US 11,179,311 B2
(45) Date of Patent: Nov. 23, 2021

(54) TRYPSIN ISOFORMS AND THEIR USE

(71) Applicant: ENZYMATICA AB, Lund (SE)

(72) Inventors: Agusta Gudmundsdottir, Reykjavik (IS); Asgeir Asgeirsson, Reykjavik (IS); Bjarki Stefansson, Reykjavik (IS)

(73) Assignee: ENZYMATICA AB, Lund (SE)

( * ) Notice: Subject to any disclaimer, the term of this patent is extended or adjusted under 35 U.S.C. 154(b) by 98 days.

(21) Appl. No.: 15/746,897

(22) PCT Filed: Jul. 22, 2016

(86) PCT No.: PCT/EP2016/067531
§ 371 (c)(1),
(2) Date: Jan. 23, 2018

(87) PCT Pub. No.: WO2017/017012
PCT Pub. Date: Feb. 2, 2017

(65) Prior Publication Data
US 2020/0197288 A1 Jun. 25, 2020

(30) Foreign Application Priority Data

Jul. 24, 2015 (EP) ..................................... 15178208

(51) Int. Cl.
| | |
|---|---|
| *A61K 8/66* | (2006.01) |
| *A61P 31/16* | (2006.01) |
| *A61K 38/17* | (2006.01) |
| *A61K 47/10* | (2017.01) |
| *A61Q 19/00* | (2006.01) |
| *C12N 9/76* | (2006.01) |

(52) U.S. Cl.
CPC ............ *A61K 8/66* (2013.01); *A61K 38/1706* (2013.01); *A61K 47/10* (2013.01); *A61P 31/16* (2018.01); *A61Q 19/00* (2013.01); *C12N 9/6427* (2013.01); *C12Y 304/21004* (2013.01)

(58) Field of Classification Search
CPC ...... A61K 8/66; A61K 38/1706; A61K 47/10; A61K 38/00; A61P 31/16; A61P 9/00; A61P 37/06; A61P 37/02; A61P 33/02; A61P 33/00; A61P 31/12; A61P 31/10; A61P 31/04; A61P 11/00; A61P 17/02; A61P 17/04; A61P 17/06; A61P 17/12; A61P 19/02; A61P 21/00; A61P 25/04; A61P 29/00; A61Q 19/00; C12N 9/6427; C12Y 304/21004
USPC ..................................................... 424/94.64
See application file for complete search history.

(56) References Cited

U.S. PATENT DOCUMENTS

| | | | |
|---|---|---|---|
| 4,801,451 A | 1/1989 | Hellgren et al. | |
| 4,963,491 A | 10/1990 | Hellgren et al. | |
| 6,846,485 B2 * | 1/2005 | Bjarnason ............... | A61P 37/00 424/94.64 |

FOREIGN PATENT DOCUMENTS

| | | |
|---|---|---|
| EP | 0 170 115 A1 | 2/1986 |
| JP | 2003-502071 | 1/2003 |
| JP | 2013-511555 | 4/2013 |
| JP | 2014-520098 | 8/2014 |
| RU | 2264824 C2 | 11/2005 |
| RU | 2286171 C1 | 10/2006 |
| WO | WO 85/04809 | 11/1985 |
| WO | WO 96/24371 | 8/1996 |
| WO | WO 00/78332 A2 | 12/2000 |
| WO | WO 2011/063394 | 5/2011 |
| WO | WO 2012/164380 | 12/2012 |
| WO | WO 2017/017012 | 2/2017 |

OTHER PUBLICATIONS

Spilliaert, R. et al. (Spilliaert, R., Gudmundsdottir, Á. Atlantic Cod Trypsin Y—Member of a Novel Trypsin Group. Marine Biotechnology. 1, 598-607 (1999). https://doi.org/10.1007/PL00011815 (Year: 1999).*
Spilliaert, R. et al. "Atlantic Cod Trypsin Y—Member of a Novel Trypsin Group." Marine Biotechnology. 1: 598-607 (1999). (Year: 1999).*
Spilliaert Tryspin Y amino acid sequence alignment with Seq ID No. 1 (Year: 1999).*
Spilliaert Tryspin Y amino acid sequence alignment with Seq ID No. 2 (Year: 1999).*
Spilliaert Tryspin Y amino acid sequence alignment with Seq ID No. 3 (Year: 1999).*
Spilliaert Tryspin Y amino acid sequence alignment with Seq ID No. 4 (Year: 1999).*
Spilliaert Tryspin Y amino acid sequence alignment with Seq ID No. 5 (Year: 1999).*
Daniels et al "A Very Late Viral Protein Triggers the Lytic Release of SV40," 2007, PLoS Pathog 3(7) e98.
Elliot and O'Hare, "Intercellular Trafficking and Protein Delivery by a Herpesvirus Structural Protein," Jan. 24, 1997, Cell, vol. 88, 223-233.
Fentress et al. "The Arginine-rich N-terminal Domain of ROP18 is Necessary for Vacuole Targeting and Virulence of Toxoplasma Gondii," Sep. 20, 2012, Cell Microbiol 14(12) 1921-1933.
GenBank entry CAD30563.1, trypsinogen Y precursor, partial [Gadus morhua].
Galdiero et al., "Microbe-Host Interactions: Structure and Role Gram-Negative Bacterial Porins," 2012, Curr Protein Pept Sci 13 843-854.
Gallaher and Garry, "Modeling of the Ebola Virus Delta Peptide Reveals a Potential Lytic Sequence Motif," 2015, Viruses 7 285-305.
Godet et al., "PP2A$_1$ Binding, Cell Transducing and Apoptotic Properties of Vpr$_{77-92}$: A New Functional Domain of HIV-1 Vpr Proteins," 2010, PLoS One 5(11) el3760.
International Search Report for PCT/EP2016/067531, dated Sep. 27, 2016, 2pgs.
Jiang et al., "Hepatitis C Virus Attachment Mediated by Apolipoprotein E Binding to Cell Surface Heparan Sulfate," 2012, J Virol, vol. 86, No. 13, 7256-7267.

(Continued)

*Primary Examiner* — Blaine Lankford
(74) *Attorney, Agent, or Firm* — Parker Highlander PLLC

(57) ABSTRACT

The present invention relates to the novel trypsin ZT isoforms. In particular, the invention relates to the use of trypsin ZT isoforms in medical devices, pharmaceuticals and cosmetics.

19 Claims, 3 Drawing Sheets
Specification includes a Sequence Listing.

(56) References Cited

OTHER PUBLICATIONS

Kang et al., "Small potassium ion channel proteins encoded by chlorella viruses," Apr. 13, 2004, Proc Natl Acad Sci USA, vol. 101, No. 15, 5318-5324.
Langedijk, "Translocation Activity of C-terminal Domain of Pestivirus Erns and Ribotoxin L3 Loop*" Feb. 15, 2002, J Biol Chem, vol. 277, No. 7, 5308-5314.
Langedijk et al., "Application, efficiency and cargo-dependence of transport peptides," 2005, International Congress Series 1277 95-107.
Liao et al., "Viroporin Activity Of SARS-CoV E Protein," 2006, Adv Exp Med Biol 581 199-202.
Lu, Tager et al., "A cell-penetrating peptide derived from mammalian cell uptake protein of *Mycobacterium tuberculosis*," 2006, Anal Biochem 353 7-14.
Milletti, "Cell-penetrating Peptides: classes, origin, and current landscape," 2012, Drug Discov Today, vol. 17, Nos. 15-16, 850-860.
O'Donoghue et al., "Global identification of peptidase specificity by multiplex substrate profiling," 2012, Nat Methods, vol. 9, No. 11, 1095-1100.
Oess and Hildt, "Novel cell permeable motif derived from the PreS2-domain of hepatitis-B virus surface antigens," 2000, Gene Ther 7 750-758.
Olsen et al., "Trypsin Cleaves Exclusively C-terminal to Arginine and Lysine Residues*," 2004, Mol Cell Proteomics 3.6, 608-614.
Overkamp et al., "Production of Polyclonal Antibodies in Ascitic Fluid of Mice: Technique and Applications," 1988, J Immunoassay 9(1), 51-68.
Palsdottir and Gudmundsdottir, "Expression and puriWcation of a cold-adapted group III trypsin in *Escherichia coli*," 2007, Protein Expr Purif 51, 243-252.
Palsdottir and Gudmundsdottir, "The novel trypsin Y from Atlantic cod (*Gadus morhua*)—isolation, purification and characterization," 2008, Food Chemistry 111 408-414.
Racaniello, "*Picornaviridae*: The Viruses and Their Replication," 2007, Fields virology, 5th ed 795-838.
Reed and Muench, 1938, "The American Journal of Hygiene" vol. 27, No. 3, 493-497.
Royle et al., "Emerging Roles of Viroporins Encoded by DNA Viruses: Novel Targets for Antivirals?" 2015, Viruses, 7, 5375-5387.
Schechter and Berger, "On The Size Of The Active Site In Proteases. I. Papain," 1967, Biochem Biophys Res Commun, vol. 27, No. 2, 157-162.
Schechter and Berger, "On The Active Site Of Proteases. III. Mapping The Active Site of Papain; Specific Peptide Inhibitors Of Papain," 1968, Biochem Biophys Res Commun, vol. 32, No. 5, 898-902.
Spilliaert et al "Atlantic cod trypsin Y—member of a novel trypsin group", Marine Biotechnology, Springer Verlag, New York, NY, US, pp. 598-607, (Jan. 1, 1999), ISSN 1436-4228, XP009187291.
Suzuki et al., "The Human Polyoma JC Virus Agnoprotein Acts as a Viroporin," 2010, PLoS Pathog 6(3) e1000801.
UniProtKB/Swiss-Prot: Q8JFQ7, dated Nov. 28, 2006.
Grishina, Zoryana, et al. "Activity of recombinant trypsin isoforms on human proteinase-activated receptors (PAR): mesotrypsin cannot activate epithelial PAR-1,-2, but weakly activates brain PAR-1." *British journal of pharmacology* 146.7 (2005): 990-999.
Office Communication issued in Russian Application No. 2018106533, dated Feb. 20, 2020. English Translation.

* cited by examiner

SEQUENCE LISTING

```
<160> NUMBER OF SEQ ID NOS: 23

<210> SEQ ID NO 1
<211> LENGTH: 227
<212> TYPE: PRT
<213> ORGANISM: Artificial Sequence
<220> FEATURE:
<223> OTHER INFORMATION: Synthetic generic sequence
<220> FEATURE:
<221> NAME/KEY: MISC_FEATURE
<222> LOCATION: (2)..(2)
<223> OTHER INFORMATION: Xaa can be I or V
<220> FEATURE:
<221> NAME/KEY: MISC_FEATURE
<222> LOCATION: (5)..(5)
<223> OTHER INFORMATION: Xaa can be Q or H
<220> FEATURE:
<221> NAME/KEY: MISC_FEATURE
<222> LOCATION: (6)..(6)
<223> OTHER INFORMATION: Xaa can be D or E
<220> FEATURE:
<221> NAME/KEY: MISC_FEATURE
<222> LOCATION: (10)..(10)
<223> OTHER INFORMATION: Xaa can be R or N
<220> FEATURE:
<221> NAME/KEY: MISC_FEATURE
<222> LOCATION: (77)..(77)
<223> OTHER INFORMATION: Xaa is L
<220> FEATURE:
<221> NAME/KEY: MISC_FEATURE
<222> LOCATION: (148)..(148)
<223> OTHER INFORMATION: Xaa can be T or P
<220> FEATURE:
<221> NAME/KEY: MISC_FEATURE
<222> LOCATION: (150)..(150)
<223> OTHER INFORMATION: Xaa can be D or A
<220> FEATURE:
<221> NAME/KEY: MISC_FEATURE
<222> LOCATION: (152)..(152)
<223> OTHER INFORMATION: Xaa can be E or Q
<220> FEATURE:
<221> NAME/KEY: MISC_FEATURE
<222> LOCATION: (154)..(154)
<223> OTHER INFORMATION: Xaa can be A or S
<220> FEATURE:
<221> NAME/KEY: MISC_FEATURE
<222> LOCATION: (164)..(164)
<223> OTHER INFORMATION: Xaa can be V or M
<220> FEATURE:
<221> NAME/KEY: MISC_FEATURE
<222> LOCATION: (166)..(166)
<223> OTHER INFORMATION: Xaa can be A or V
<220> FEATURE:
<221> NAME/KEY: MISC_FEATURE
<222> LOCATION: (168)..(168)
<223> OTHER INFORMATION: Xaa can be Y or F
<220> FEATURE:
<221> NAME/KEY: MISC_FEATURE
<222> LOCATION: (175)..(175)
<223> OTHER INFORMATION: Xaa can be A or V
<220> FEATURE:
<221> NAME/KEY: MISC_FEATURE
<222> LOCATION: (198)..(198)
<223> OTHER INFORMATION: Xaa can be Q or R
<220> FEATURE:
<221> NAME/KEY: MISC_FEATURE
```

```
<222> LOCATION: (202)..(202)
<223> OTHER INFORMATION: Xaa can be L or E
<220> FEATURE:
<221> NAME/KEY: MISC_FEATURE
<222> LOCATION: (205)..(205)
<223> OTHER INFORMATION: Xaa can be Y or S
<220> FEATURE:
<221> NAME/KEY: MISC_FEATURE
<222> LOCATION: (215)..(215)
<223> OTHER INFORMATION: Xaa can be Y or F

<400> SEQUENCE: 1

Ile Xaa Gly Gly Xaa Xaa Cys Glu Pro Xaa Ser Arg Pro Phe Met Ala
1               5                   10                  15

Ser Leu Asn Tyr Gly Tyr His Phe Cys Gly Gly Val Leu Ile Asn Asp
            20                  25                  30

Gln Trp Val Leu Ser Val Ala His Cys Trp Tyr Asn Pro Tyr Tyr Met
        35                  40                  45

Gln Val Met Leu Gly Glu His Asp Leu Arg Val Phe Glu Gly Thr Glu
    50                  55                  60

Gln Leu Val Lys Thr Asn Thr Ile Phe Trp His Glu Xaa Tyr Asp Tyr
65                  70                  75                  80

Gln Thr Leu Asp Tyr Asp Met Met Met Ile Lys Leu Tyr His Pro Val
                85                  90                  95

Glu Val Thr Gln Ser Val Ala Pro Ile Ser Leu Pro Thr Gly Pro Pro
            100                 105                 110

Asp Gly Gly Met Leu Cys Ser Val Ser Gly Trp Gly Asn Met Ala Met
        115                 120                 125

Gly Glu Glu Val Asn Leu Pro Thr Arg Leu Gln Cys Leu Asp Val Pro
130                 135                 140

Ile Val Glu Xaa Val Xaa Cys Xaa Ala Xaa Tyr Pro Gly Met Ile Ser
145                 150                 155                 160

Pro Arg Met Xaa Cys Xaa Gly Xaa Met Asp Gly Gly Arg Asp Xaa Cys
                165                 170                 175

Asn Gly Asp Ser Gly Ser Pro Leu Val Cys Glu Gly Val Leu Thr Gly
            180                 185                 190

Leu Val Ser Trp Gly Xaa Gly Cys Ala Xaa Pro Asn Xaa Pro Gly Val
        195                 200                 205

Tyr Val Lys Val Tyr Glu Xaa Leu Ser Trp Ile Gln Thr Thr Leu Asp
    210                 215                 220

Ala Asn Pro
225

<210> SEQ ID NO 2
<211> LENGTH: 227
<212> TYPE: PRT
<213> ORGANISM: Gadus morhua

<400> SEQUENCE: 2

Ile Val Gly Gly His Glu Cys Glu Pro Asn Ser Arg Pro Phe Met Ala
1               5                   10                  15

Ser Leu Asn Tyr Gly Tyr His Phe Cys Gly Gly Val Leu Ile Asn Asp
            20                  25                  30

Gln Trp Val Leu Ser Val Ala His Cys Trp Tyr Asn Pro Tyr Tyr Met
        35                  40                  45

Gln Val Met Leu Gly Glu His Asp Leu Arg Val Phe Glu Gly Thr Glu
    50                  55                  60

Gln Leu Val Lys Thr Asn Thr Ile Phe Trp His Glu Leu Tyr Asp Tyr
```

```
            65                  70                  75                  80
        Gln Thr Leu Asp Tyr Asp Met Met Ile Lys Leu Tyr His Pro Val
                        85                  90                  95
        Glu Val Thr Gln Ser Val Ala Pro Ile Ser Leu Pro Thr Gly Pro Pro
                        100                 105                 110
        Asp Gly Gly Met Leu Cys Ser Val Ser Gly Trp Gly Asn Met Ala Met
                        115                 120                 125
        Gly Glu Glu Val Asn Leu Pro Thr Arg Leu Gln Cys Leu Asp Val Pro
                130                 135                 140
        Ile Val Glu Pro Val Ala Cys Gln Ala Ser Tyr Pro Gly Met Ile Ser
        145                 150                 155                 160
        Pro Arg Met Met Cys Val Gly Phe Met Asp Gly Gly Arg Asp Val Cys
                                165                 170                 175
        Asn Gly Asp Ser Gly Ser Pro Leu Val Cys Glu Gly Val Leu Thr Gly
                                180                 185                 190
        Leu Val Ser Trp Gly Arg Gly Cys Ala Glu Pro Asn Ser Pro Gly Val
                                195                 200                 205
        Tyr Val Lys Val Tyr Glu Phe Leu Ser Trp Ile Gln Thr Thr Leu Asp
                                210                 215                 220
        Ala Asn Pro
        225
```

<210> SEQ ID NO 3
<211> LENGTH: 227
<212> TYPE: PRT
<213> ORGANISM: Gadus morhua

<400> SEQUENCE: 3

```
        Ile Val Gly Gly His Glu Cys Glu Pro Asn Ser Arg Pro Phe Met Ala
        1               5                   10                  15
        Ser Leu Asn Tyr Gly Tyr His Phe Cys Gly Gly Val Leu Ile Asn Asp
                        20                  25                  30
        Gln Trp Val Leu Ser Val Ala His Cys Trp Tyr Asn Pro Tyr Tyr Met
                        35                  40                  45
        Gln Val Met Leu Gly Glu His Asp Leu Arg Val Phe Glu Gly Thr Glu
                50                  55                  60
        Gln Leu Val Lys Thr Asn Thr Ile Phe Trp His Glu Leu Tyr Asp Tyr
        65                  70                  75                  80
        Gln Thr Leu Asp Tyr Asp Met Met Met Ile Lys Leu Tyr His Pro Val
                        85                  90                  95
        Glu Val Thr Gln Ser Val Ala Pro Ile Ser Leu Pro Thr Gly Pro Pro
                        100                 105                 110
        Asp Gly Gly Met Leu Cys Ser Val Ser Gly Trp Gly Asn Met Ala Met
                        115                 120                 125
        Gly Glu Glu Val Asn Leu Pro Thr Arg Leu Gln Cys Leu Asp Val Pro
                130                 135                 140
        Ile Val Glu Thr Val Asp Cys Glu Ala Ala Tyr Pro Gly Met Ile Ser
        145                 150                 155                 160
        Pro Arg Met Val Cys Ala Gly Tyr Met Asp Gly Gly Arg Asp Ala Cys
                                165                 170                 175
        Asn Gly Asp Ser Gly Ser Pro Leu Val Cys Glu Gly Val Leu Thr Gly
                                180                 185                 190
        Leu Val Ser Trp Gly Gln Gly Cys Ala Leu Pro Asn Tyr Pro Gly Val
                                195                 200                 205
```

Tyr Val Lys Val Tyr Glu Tyr Leu Ser Trp Ile Gln Thr Thr Leu Asp
    210                 215                 220

Ala Asn Pro
225

<210> SEQ ID NO 4
<211> LENGTH: 227
<212> TYPE: PRT
<213> ORGANISM: Gadus morhua

<400> SEQUENCE: 4

Ile Ile Gly Gly Gln Asp Cys Glu Pro Arg Ser Arg Pro Phe Met Ala
1               5                   10                  15

Ser Leu Asn Tyr Gly Tyr His Phe Cys Gly Gly Val Leu Ile Asn Asp
            20                  25                  30

Gln Trp Val Leu Ser Val Ala His Cys Trp Tyr Asn Pro Tyr Tyr Met
        35                  40                  45

Gln Val Met Leu Gly Glu His Asp Leu Arg Val Phe Glu Gly Thr Glu
    50                  55                  60

Gln Leu Val Lys Thr Asn Thr Ile Phe Trp His Glu Leu Tyr Asp Tyr
65                  70                  75                  80

Gln Thr Leu Asp Tyr Asp Met Met Met Ile Lys Leu Tyr His Pro Val
                85                  90                  95

Glu Val Thr Gln Ser Val Ala Pro Ile Ser Leu Pro Thr Gly Pro Pro
            100                 105                 110

Asp Gly Gly Met Leu Cys Ser Val Ser Gly Trp Gly Asn Met Ala Met
        115                 120                 125

Gly Glu Glu Val Asn Leu Pro Thr Arg Leu Gln Cys Leu Asp Val Pro
    130                 135                 140

Ile Val Glu Pro Val Ala Cys Gln Ala Ser Tyr Pro Gly Met Ile Ser
145                 150                 155                 160

Pro Arg Met Met Cys Val Gly Phe Met Asp Gly Gly Arg Asp Val Cys
                165                 170                 175

Asn Gly Asp Ser Gly Ser Pro Leu Val Cys Glu Gly Val Leu Thr Gly
            180                 185                 190

Leu Val Ser Trp Gly Arg Gly Cys Ala Glu Pro Asn Ser Pro Gly Val
        195                 200                 205

Tyr Val Lys Val Tyr Glu Phe Leu Ser Trp Ile Gln Thr Thr Leu Asp
    210                 215                 220

Ala Asn Pro
225

<210> SEQ ID NO 5
<211> LENGTH: 227
<212> TYPE: PRT
<213> ORGANISM: Gadus morhua

<400> SEQUENCE: 5

Ile Ile Gly Gly Gln Asp Cys Glu Pro Arg Ser Arg Pro Phe Met Ala
1               5                   10                  15

Ser Leu Asn Tyr Gly Tyr His Phe Cys Gly Gly Val Leu Ile Asn Asp
            20                  25                  30

Gln Trp Val Leu Ser Val Ala His Cys Trp Tyr Asn Pro Tyr Tyr Met
        35                  40                  45

Gln Val Met Leu Gly Glu His Asp Leu Arg Val Phe Glu Gly Thr Glu
    50                  55                  60

```
Gln Leu Val Lys Thr Asn Thr Ile Phe Trp His Glu Leu Tyr Asp Tyr
 65                  70                  75                  80

Gln Thr Leu Asp Tyr Asp Met Met Ile Lys Leu Tyr His Pro Val
                 85                  90                  95

Glu Val Thr Gln Ser Val Ala Pro Ile Ser Leu Pro Thr Gly Pro Pro
            100                 105                 110

Asp Gly Gly Met Leu Cys Ser Val Ser Gly Trp Gly Asn Met Ala Met
            115                 120                 125

Gly Glu Glu Val Asn Leu Pro Thr Arg Leu Gln Cys Leu Asp Val Pro
130                 135                 140

Ile Val Glu Thr Val Asp Cys Glu Ala Ala Tyr Pro Gly Met Ile Ser
145                 150                 155                 160

Pro Arg Met Val Cys Ala Gly Tyr Met Asp Gly Gly Arg Asp Ala Cys
                165                 170                 175

Asn Gly Asp Ser Gly Ser Pro Leu Val Cys Glu Gly Val Leu Thr Gly
            180                 185                 190

Leu Val Ser Trp Gly Gln Gly Cys Ala Leu Pro Asn Tyr Pro Gly Val
            195                 200                 205

Tyr Val Lys Val Tyr Glu Tyr Leu Ser Trp Ile Gln Thr Thr Leu Asp
        210                 215                 220

Ala Asn Pro
225

<210> SEQ ID NO 6
<211> LENGTH: 10
<212> TYPE: PRT
<213> ORGANISM: Artificial Sequence
<220> FEATURE:
<223> OTHER INFORMATION: Synthetic peptide Fragment 1

<400> SEQUENCE: 6

Ile Ile Gly Gly Gln Asp Cys Glu Pro Arg
1               5                   10

<210> SEQ ID NO 7
<211> LENGTH: 10
<212> TYPE: PRT
<213> ORGANISM: Artificial Sequence
<220> FEATURE:
<223> OTHER INFORMATION: Synthetic peptide Fragment 2

<400> SEQUENCE: 7

Val Phe Glu Gly Thr Glu Gln Leu Val Lys
1               5                   10

<210> SEQ ID NO 8
<211> LENGTH: 25
<212> TYPE: PRT
<213> ORGANISM: Artificial Sequence
<220> FEATURE:
<223> OTHER INFORMATION: Synthetic peptide Fragment 3

<400> SEQUENCE: 8

Leu Gln Cys Leu Asp Val Pro Ile Val Glu Pro Val Ala Cys Gln Ala
1               5                   10                  15

Ser Tyr Pro Gly Met Ile Ser Pro Arg
            20                  25

<210> SEQ ID NO 9
<211> LENGTH: 25
<212> TYPE: PRT
```

-continued

```
<213> ORGANISM: Artificial Sequence
<220> FEATURE:
<223> OTHER INFORMATION: Synthetic peptide Fragment 4

<400> SEQUENCE: 9

Leu Gln Cys Leu Asp Val Pro Ile Val Glu Thr Val Asp Cys Glu Ala
1               5                   10                  15

Ala Tyr Pro Gly Met Ile Ser Pro Arg
            20                  25

<210> SEQ ID NO 10
<211> LENGTH: 11
<212> TYPE: PRT
<213> ORGANISM: Artificial Sequence
<220> FEATURE:
<223> OTHER INFORMATION: Synthetic peptide Fragment 5

<400> SEQUENCE: 10

Met Val Cys Ala Gly Tyr Met Asp Gly Gly Arg
1               5                   10

<210> SEQ ID NO 11
<211> LENGTH: 11
<212> TYPE: PRT
<213> ORGANISM: Artificial Sequence
<220> FEATURE:
<223> OTHER INFORMATION: Synthetic peptide Fragment 6

<400> SEQUENCE: 11

Met Met Cys Val Gly Phe Met Asp Gly Gly Arg
1               5                   10

<210> SEQ ID NO 12
<211> LENGTH: 13
<212> TYPE: PRT
<213> ORGANISM: Artificial Sequence
<220> FEATURE:
<223> OTHER INFORMATION: Synthetic peptide Fragment 7

<400> SEQUENCE: 12

Gly Cys Ala Glu Pro Asn Ser Pro Gly Val Tyr Val Lys
1               5                   10

<210> SEQ ID NO 13
<211> LENGTH: 25
<212> TYPE: PRT
<213> ORGANISM: Artificial Sequence
<220> FEATURE:
<223> OTHER INFORMATION: Synthetic peptide Fragment 8

<400> SEQUENCE: 13

Asp Val Cys Asn Gly Asp Ser Gly Ser Pro Leu Val Cys Glu Gly Val
1               5                   10                  15

Leu Thr Gly Leu Val Ser Trp Gly Arg
            20                  25

<210> SEQ ID NO 14
<211> LENGTH: 6
<212> TYPE: PRT
<213> ORGANISM: Artificial Sequence
<220> FEATURE:
<223> OTHER INFORMATION: Synthetic peptide Fragment 9

<400> SEQUENCE: 14

Gln Gly Lys Lys Ala Pro
1               5
```

<210> SEQ ID NO 15
<211> LENGTH: 8
<212> TYPE: PRT
<213> ORGANISM: Artificial Sequence
<220> FEATURE:
<223> OTHER INFORMATION: Synthetic peptide Fragment 10

<400> SEQUENCE: 15

Trp Gly Asn Arg Ser Pro Leu Glu
1               5

<210> SEQ ID NO 16
<211> LENGTH: 8
<212> TYPE: PRT
<213> ORGANISM: Artificial Sequence
<220> FEATURE:
<223> OTHER INFORMATION: Synthetic peptide Fragment 11

<400> SEQUENCE: 16

Gln Ala Val Arg Pro Asn Gly Met
1               5

<210> SEQ ID NO 17
<211> LENGTH: 8
<212> TYPE: PRT
<213> ORGANISM: Artificial Sequence
<220> FEATURE:
<223> OTHER INFORMATION: Synthetic peptide Fragment 12

<400> SEQUENCE: 17

Phe Asp Asn Arg Val Gly Lys Trp
1               5

<210> SEQ ID NO 18
<211> LENGTH: 7
<212> TYPE: PRT
<213> ORGANISM: Artificial Sequence
<220> FEATURE:
<223> OTHER INFORMATION: Synthetic peptide Fragment 13

<400> SEQUENCE: 18

Ile Ala Arg Gln Pro Trp Asn
1               5

<210> SEQ ID NO 19
<211> LENGTH: 250
<212> TYPE: PRT
<213> ORGANISM: Gadus morhua

<400> SEQUENCE: 19

Met Ile Gly Leu Ala Leu Leu Met Leu Leu Gly Ala Ala Ala Ala Ala
1               5                   10                  15

Val Pro Arg Asp Val Gly Lys Ile Val Gly Gly His Glu Cys Glu Pro
            20                  25                  30

Asn Ser Arg Pro Phe Met Ala Ser Leu Asn Tyr Gly Tyr His Phe Cys
        35                  40                  45

Gly Gly Val Leu Ile Asn Asp Gln Trp Val Leu Ser Val Ala His Cys
    50                  55                  60

Trp Tyr Asn Pro Tyr Tyr Met Gln Val Met Leu Gly Glu His Asp Leu
65              70                  75                  80

Arg Val Phe Glu Gly Thr Glu Gln Leu Val Lys Thr Asn Thr Ile Phe
                85                  90                  95

```
Trp His Glu Leu Tyr Asp Tyr Gln Thr Leu Asp Tyr Asp Met Met Met
            100                 105                 110

Ile Lys Leu Tyr His Pro Val Glu Val Thr Gln Ser Val Ala Pro Ile
            115                 120                 125

Ser Leu Pro Thr Gly Pro Pro Asp Gly Gly Met Leu Cys Ser Val Ser
130                 135                 140

Gly Trp Gly Asn Met Ala Met Gly Glu Glu Val Asn Leu Pro Thr Arg
145                 150                 155                 160

Leu Gln Cys Leu Asp Val Pro Ile Val Glu Pro Val Ala Cys Gln Ala
                165                 170                 175

Ser Tyr Pro Gly Met Ile Ser Pro Arg Met Met Cys Val Gly Phe Met
            180                 185                 190

Asp Gly Gly Arg Asp Val Cys Asn Gly Asp Ser Gly Ser Pro Leu Val
            195                 200                 205

Cys Glu Gly Val Leu Thr Gly Leu Val Ser Trp Gly Arg Gly Cys Ala
210                 215                 220

Glu Pro Asn Ser Pro Gly Val Tyr Val Lys Val Tyr Glu Phe Leu Ser
225                 230                 235                 240

Trp Ile Gln Thr Thr Leu Asp Ala Asn Pro
            245                 250

<210> SEQ ID NO 20
<211> LENGTH: 250
<212> TYPE: PRT
<213> ORGANISM: Gadus morhua

<400> SEQUENCE: 20

Met Ile Gly Leu Ala Leu Leu Met Leu Leu Gly Ala Ala Ala Ala Ala
1               5                   10                  15

Val Pro Arg Asp Val Gly Lys Ile Val Gly Gly His Glu Cys Glu Pro
            20                  25                  30

Asn Ser Arg Pro Phe Met Ala Ser Leu Asn Tyr Gly Tyr His Phe Cys
        35                  40                  45

Gly Gly Val Leu Ile Asn Asp Gln Trp Val Leu Ser Val Ala His Cys
50                  55                  60

Trp Tyr Asn Pro Tyr Tyr Met Gln Val Met Leu Gly Glu His Asp Leu
65                  70                  75                  80

Arg Val Phe Glu Gly Thr Glu Gln Leu Val Lys Thr Asn Thr Ile Phe
                85                  90                  95

Trp His Glu Leu Tyr Asp Tyr Gln Thr Leu Asp Tyr Asp Met Met Met
            100                 105                 110

Ile Lys Leu Tyr His Pro Val Glu Val Thr Gln Ser Val Ala Pro Ile
            115                 120                 125

Ser Leu Pro Thr Gly Pro Pro Asp Gly Gly Met Leu Cys Ser Val Ser
130                 135                 140

Gly Trp Gly Asn Met Ala Met Gly Glu Glu Val Asn Leu Pro Thr Arg
145                 150                 155                 160

Leu Gln Cys Leu Asp Val Pro Ile Val Glu Thr Val Asp Cys Glu Ala
                165                 170                 175

Ala Tyr Pro Gly Met Ile Ser Pro Arg Met Val Cys Ala Gly Tyr Met
            180                 185                 190

Asp Gly Gly Arg Asp Ala Cys Asn Gly Asp Ser Gly Ser Pro Leu Val
            195                 200                 205

Cys Glu Gly Val Leu Thr Gly Leu Val Ser Trp Gly Gln Gly Cys Ala
210                 215                 220
```

Leu Pro Asn Tyr Pro Gly Val Tyr Val Lys Val Tyr Glu Tyr Leu Ser
225                 230                 235                 240

Trp Ile Gln Thr Thr Leu Asp Ala Asn Pro
                245                 250

<210> SEQ ID NO 21
<211> LENGTH: 249
<212> TYPE: PRT
<213> ORGANISM: Gadus morhua

<400> SEQUENCE: 21

Met Ile Gly Leu Ala Leu Leu Met Leu Leu Gly Ala Ala Ala Val
1               5                   10                  15

Pro Arg Glu Asp Gly Arg Ile Ile Gly Gly Gln Asp Cys Glu Pro Arg
                20                  25                  30

Ser Arg Pro Phe Met Ala Ser Leu Asn Tyr Gly Tyr His Phe Cys Gly
            35                  40                  45

Gly Val Leu Ile Asn Asp Gln Trp Val Leu Ser Val Ala His Cys Trp
    50                  55                  60

Tyr Asn Pro Tyr Met Gln Val Met Leu Gly Glu His Asp Leu Arg
65                  70                  75                  80

Val Phe Glu Gly Thr Glu Gln Leu Val Lys Thr Asn Thr Ile Phe Trp
                85                  90                  95

His Glu Leu Tyr Asp Tyr Gln Thr Leu Asp Tyr Asp Met Met Met Ile
            100                 105                 110

Lys Leu Tyr His Pro Val Glu Val Thr Gln Ser Val Ala Pro Ile Ser
        115                 120                 125

Leu Pro Thr Gly Pro Pro Asp Gly Gly Met Leu Cys Ser Val Ser Gly
    130                 135                 140

Trp Gly Asn Met Ala Met Gly Glu Glu Val Asn Leu Pro Thr Arg Leu
145                 150                 155                 160

Gln Cys Leu Asp Val Pro Ile Val Glu Pro Val Ala Cys Gln Ala Ser
                165                 170                 175

Tyr Pro Gly Met Ile Ser Pro Arg Met Met Cys Val Gly Phe Met Asp
            180                 185                 190

Gly Gly Arg Asp Val Cys Asn Gly Asp Ser Gly Ser Pro Leu Val Cys
        195                 200                 205

Glu Gly Val Leu Thr Gly Leu Val Ser Trp Gly Arg Gly Cys Ala Glu
    210                 215                 220

Pro Asn Ser Pro Gly Val Tyr Val Lys Val Tyr Glu Phe Leu Ser Trp
225                 230                 235                 240

Ile Gln Thr Thr Leu Asp Ala Asn Pro
                245

<210> SEQ ID NO 22
<211> LENGTH: 249
<212> TYPE: PRT
<213> ORGANISM: Gadus morhua

<400> SEQUENCE: 22

Met Ile Gly Leu Ala Leu Leu Met Leu Leu Gly Ala Ala Ala Val
1               5                   10                  15

Pro Arg Glu Asp Gly Arg Ile Ile Gly Gly Gln Asp Cys Glu Pro Arg
                20                  25                  30

Ser Arg Pro Phe Met Ala Ser Leu Asn Tyr Gly Tyr His Phe Cys Gly
            35                  40                  45

```
Gly Val Leu Ile Asn Asp Gln Trp Val Leu Ser Val Ala His Cys Trp
    50                  55                  60

Tyr Asn Pro Tyr Tyr Met Gln Val Met Leu Gly Glu His Asp Leu Arg
65                  70                  75                  80

Val Phe Glu Gly Thr Glu Gln Leu Val Lys Thr Asn Thr Ile Phe Trp
                85                  90                  95

His Glu Leu Tyr Asp Tyr Gln Thr Leu Asp Tyr Asp Met Met Met Ile
                100                 105                 110

Lys Leu Tyr His Pro Val Glu Val Thr Gln Ser Val Ala Pro Ile Ser
            115                 120                 125

Leu Pro Thr Gly Pro Pro Asp Gly Gly Met Leu Cys Ser Val Ser Gly
        130                 135                 140

Trp Gly Asn Met Ala Met Gly Glu Glu Val Asn Leu Pro Thr Arg Leu
145                 150                 155                 160

Gln Cys Leu Asp Val Pro Ile Val Glu Thr Val Asp Cys Glu Ala Ala
                165                 170                 175

Tyr Pro Gly Met Ile Ser Pro Arg Met Val Cys Ala Gly Tyr Met Asp
                180                 185                 190

Gly Gly Arg Asp Ala Cys Asn Gly Asp Ser Gly Ser Pro Leu Val Cys
            195                 200                 205

Glu Gly Val Leu Thr Gly Leu Val Ser Trp Gly Gln Gly Cys Ala Leu
        210                 215                 220

Pro Asn Tyr Pro Gly Val Tyr Val Lys Val Tyr Glu Tyr Leu Ser Trp
225                 230                 235                 240

Ile Gln Thr Thr Leu Asp Ala Asn Pro
                245

<210> SEQ ID NO 23
<211> LENGTH: 12
<212> TYPE: PRT
<213> ORGANISM: Gadus morhua

<400> SEQUENCE: 23

Cys Val Leu Ser Gly Trp Val Arg Asp Thr Met Ala
1               5                   10
```

TRYPSIN ISOFORMS AND THEIR USE

This application is a national phase application under 35 U.S.C. § 371 of International Application No. PCT/EP2016/067531, filed Jul. 22, 2016, which claims priority to European Patent Application No. 15178208.3 filed Jul. 24, 2015. The entire text of each of the above referenced disclosures is specifically incorporated herein by reference.

FIELD OF THE INVENTION

The present invention relates to the novel trypsin ZT isoforms. In particular, the invention relates to the use of trypsin ZT isoforms in medical devices, pharmaceuticals and cosmetics.

BACKGROUND OF THE INVENTION

Proteinases are enzymes that are defined by their ability to cleave proteins. Proteinases can cleave substrates at different amino residues within a protein sequence demonstrating a difference in substrate specificity. Trypsins are proteinases and are partly specified by their preference in cleaving C-terminal to arginine or lysine residues (Olsen, Ong et al., 2004, *Mol Cell Proteomics* 3: 608-614). The Multiplex Substrate Profiling method reveals cleavage sites of proteinases and discloses the critical importance of residues surrounding their cleavage site for their specificity (O'Donoghue, Eroy-Reveles et al., 2012, *Nat Methods* 9: 1095-1100).

U.S. Pat. Nos. 4,801,451 and 4,963,491 disclose a mixture of exo- and endopeptidases isolated from Antarctic krill (*Euphasia superba*) and the use of this mixture as a cleaning solution. U.S. Pat. No. 4,801,451 discloses the use of such enzymes to remove foreign matter and dead tissue from wounds. WO 85/04809 discloses the use of krill enzymes as a digestion-promoting agent. EP-A1-0170115 discloses the use of krill enzymes to dissolve blood clots. However, all of these references disclose impure or poorly characterized materials. A purified peptidase or mixture of purified peptidases is desirable to provide a pharmaceutically useful product.

WO 96/24371 discloses the use of a krill-derived multifunctional proteolytic enzyme and a family of crustacean and fish derived proteolytic enzymes having structural similarity to the multifunctional enzyme derived from Antarctic krill. The document also relates to methods of purifying the multifunctional enzyme and to pharmaceutical, cosmetic and other uses of the multifunctional enzyme. Structural similarity to the multifunctional enzyme derived from Antarctic krill is defined in that document as at least 70% homology with the krill derived multifunctional hydrolase.

WO 2000078332 discloses the use of cod derived trypsins and chymotrypsins in pharmaceutical compositions or medicaments for local and topical application to treat internal diseases and disorders and cosmetic use of such enzymes. The topical use for treating local, internal disorders, without the enzyme having to penetrate through open wounds or mucous tissue, was found to be effective. The serine proteinases disclosed in WO 2000078332 are proteinases that have at least 90% amino acid sequence homology with trypsin I, trypsin II, trypsin III, trypsin IV derived from Atlantic cod and proteinases that are chymotrypsin having at least 90% amino acid sequence homology with any of chymotrypsin A and chymotrypsin B isolated from Atlantic cod.

A complementary DNA (cDNA) encoding trypsin Y was isolated from an Atlantic cod cDNA library (Spilliaert and Gudmundsdottir, 1999, *Mar Biotechnol* (NY) 1: 598-607). Cod trypsin Y has approximately 45% identity to the two Atlantic cod trypsin I and X (WO 2000078332). The native trypsin Y and recombinant forms of trypsin Y have previously briefly been described (Palsdottir and Gudmundsdottir, 2007, *Protein Expr Purif* 51: 243-252, Palsdottir and Gudmundsdottir, 2008, *Food Chemistry* 111: 408-414).

SUMMARY OF THE INVENTION

The present invention provides novel trypsin isoforms, called trypsin ZT isoforms. Such isoforms are derivable from fish, such as the Atlantic cod, or derivable in recombinant form using protein expression systems. The present invention further provides compositions comprising at least one isolated cod trypsin ZT isoform according to the invention, together with suitable excipients and carriers.

The inventors have identified unexpected, beneficial and unique characteristics of the novel trypsin ZT isoforms over trypsins known previously. These characteristics provide an advantage in using trypsin ZT isoforms for various applications in medical devices, pharmaceuticals and cosmetics. The present invention provides said trypsin ZT isoforms per se and for use in treating or preventing diseases caused by pathogenic organisms. This is particularly relevant for use in treating or preventing a disease in the upper respiratory tract caused by pathogenic microorganisms. For that purpose, trypsin ZT isoforms can for example be used in medical devices or as active ingredient(s) in a pharmaceutical. Also, the present invention provides said trypsin ZT isoforms for use in the treatment of wound infections and wounds from burns, for use in removing dead or peeling skin from otherwise healthy skin for example in a medical device, as a pharmaceutical or as a cosmetic. The present invention further provides methods of preparing cod trypsin ZT isoforms of the present invention.

- Based on multiplex substrate profiling, trypsin ZT isoforms prefer cleavage at Arg residues compared to trypsin I. Trypsin I prefers cleavage at Lys residues compared to trypsin ZT isoforms.
- Multiplex substrate profiling shows that different amino acid residues in the substrate surrounding the cleavage site have a large effect on cleavage (about four amino acids residues on the N terminal side and about four amino acid residues on the C terminal side). Trypsin ZT isoforms prefer certain amino acid residues surrounding the cleavage site over trypsin I.
- Arginine and lysine rich amino acid sequences are frequently found in viral-, bacterial- and parasite sequences that are associated with infection.
- Numerical values based on standard scores (Z-score) ratio (multiplex substrate profiling data) show that trypsin ZT isoforms are much better adapted to cleave peptides containing several consecutive basic amino acid residues (Arg and Lys) compared to trypsin I. Based on the data, trypsin ZT isoforms can act as antimicrobial agents against viruses and bacteria as they can cleave at clustered basic amino acid residues such as lysine and arginine.

DETAILED DESCRIPTION OF THE INVENTION

The present invention provides novel trypsin isoforms, called trypsin ZT isoforms. Such isoforms are derivable from fish, such as the Atlantic cod, or derivable in recombinant form using protein expression systems. The present invention relates to using such trypsin ZT isoforms for treatment and prevention of disease and to the cosmetic field. In particular, the invention relates to novel Atlantic cod trypsin ZT isoforms, useful as pharmaceuticals, in medical devices, and cosmetics.

Figure 1:
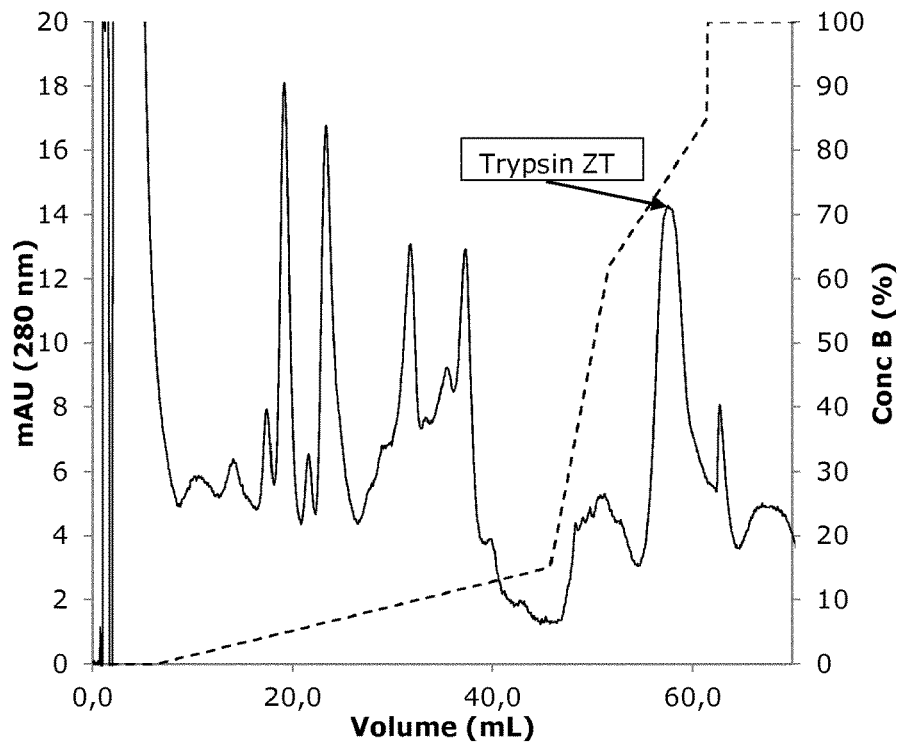
FIG. 1 shows isolation of trypsin ZT isoforms with anion exchange chromatography. Chromatogram from a MonoQ separation of benzamidine purified cod trypsin isoforms showing absorbance at 280 nm vs. elution volume. Cod trypsin isoforms were loaded on a MonoQ column and proteins eluted with a salt gradient (dotted line). Arrow shows the peak containing trypsin ZT isoforms. The column was equilibrated with a buffer (20 mM Tris, 10 mM CaCl$_2$, pH 8.0), and the enzymes were eluted with a linear 0-150 mM NaCl gradient in 40 column volumes, linear 150-620 mM NaCl in 6 column volumes, 620-850 mM NaCl in 10 column volumes at a flow rate of 1 mL/min.

The inventors have identified novel trypsin isoforms termed trypsin ZT isoforms. Trypsin ZT includes at least the following isoforms: Atlantic cod trypsin ZT-1 isoform, Atlantic cod trypsin ZT-2 isoform, Atlantic cod trypsin ZT-3 isoform and Atlantic cod trypsin ZT-4 isoform. All four Atlantic cod trypsin ZT isoforms have a similar molecular mass of about 25 kDa. The Atlantic cod trypsin ZT isoforms of the present invention are represented by the following amino acid sequences:

SEQ ID NO:1
IX$_1$GGX$_2$X$_3$CEPX$_4$SRPFMASLNYGYHFCGGVLINDQWVLSVAHCWYNPYY

MQVMLGEHDLRVFEGTEQLVKTNTIFWHEX$_5$YDYQTLDYDMMMIKLYHPV

EVTQSVAPISLPTGPPDGGMLCSVSGWGNMAMGEEVNLPTRLQCLDVPIV

EX$_6$VX$_7$CX$_8$AX$_9$YPGMISPRMX$_{10}$CX$_{11}$GX$_{12}$MDGGRDX$_{13}$CNGDSGSPLVCEG

VLTGLVSWGX$_{14}$GCAX$_{15}$PNX$_{16}$PGVYVKVYEX$_{17}$LSWIQTTLDANP $X_1$ is selected from I and V;
$X_2$ is selected from Q and H;
$X_3$ is selected from D and E;
$X_4$ is selected from R and N;
$X_5$ is L;
$X_6$ is selected from T and P;
$X_7$ is selected from D and A;
$X_9$ is selected from E and Q;
$X_9$ is selected from A and S;
$X_{10}$ is selected from V and M;
$X_{11}$ is selected from A and V;
$X_{12}$ is selected from Y and F;
$X_{13}$ is selected from A and V;
$X_{14}$ is selected from Q and R;
$X_{15}$ is selected from L and E;
$X_{16}$ is selected from Y and S; and
$X_{17}$ is selected from Y and F.

The Atlantic cod trypsin ZT-1 isoform

SEQ ID NO: 2
IVGGHECEPNSRPFMASLNYGYHFCGGVLINDQWVLSVAHCWYNPYYMQVM

LGEHDLRVFEGTEQLVKTNTIFWHELYDYQTLDYDMMMIKLYHPVEVTQSV

APISLPTGPPDGGMLCSVSGWGNMAMGEEVNLPTRLQCLDVPIVEPVACQA

SYPGMISPRMMCVGFMDGGRDVCNGDS GSPLVCEGVLTGLVSWGRGC AE

PNSPGVYVKVYEFLSWIQTTLDANP

The Atlantic cod trypsin ZT-2 isoform

SEQ ID NO: 3
IVGGHECEPNSRPFMASLNYGYHFCGGVLINDQWVLSVAHCWYNPYYMQVM

LGEHDLRVFEGTEQLVKTNTIFWHELYDYQTLDYDMMMIKLYHPVEVTQSV

APISLPTGPPDGGMLCSVSGWGNMAMGEEVNLPTRLQCLDVPIVETVDCEA

AYPGMISPRMVCAGYMDGGRDACNGDS GSPLVCEGVLTGLVSWGQGC AL

PNYPGVYVKVYEYLSWIQTTLDANP

The Atlantic cod trypsin ZT-3 isoform

SEQ ID NO: 4
IIGGQDCEPRSRPFMASLNYGYHFCGGVLINDQWVLSVAHCWYNPYYMQVM

LGEHDLRVFEGTEQLVKTNTIFWHELYDYQTLDYDMMMIKLYHPVEVTQSV

APISLPTGPPDGGMLCSVSGWGNMAMGEEVNLPTRLQCLDVPIVEPVACQA

SYPGMISPRMMCVGFMDGGRDVCNGDS GSPLVCEGVLTGLVSWGRGCAEP

NSPGVYV KVYEFLSWIQTTLDANP

The Atlantic cod trypsin ZT-4 isoform

SEQ ID NO: 5
IIGGQDCEPRSRPFMASLNYGYHFCGGVLINDQWVLSVAHCWYNPYYMQVM

LGEHDLRVFEGTEQLVKTNTIFWHELYDYQTLDYDMMMIKLYHPVEVTQSV

-continued

APISLPTGPPDGGMLCSVSGWGNMAMGEEVNLPTRLQCLDVPIVETVDCEA

AYPGMISPRMVCAGYMDGGRDACNGDSGSPLVCEGVLTGLVSWGQGC ALP

NYPGVYVKVYEYLSWIQTTLDANP

Trypsin ZT isoforms of the present invention have less than 50% amino acid identity with the trypsins disclosed in WO 2000078332 and less than 45% homology with the chymotrypsins disclosed in WO 2000078332.

The above trypsin ZT isoforms represents the active variants of these trypsins, i.e. variants that have been activated when the N terminus of the trypsins have been cleaved off. These trypsins are proteins expressed in the pyloric caeca (pancreatic tissue in fish) with a number of amino acids on the N terminal end that are important for secretion out of the cells and for keeping the enzyme inactive. The full length trypsin ZT isoforms are also disclosed herein as Uncleaved Atlantic cod trypsin ZT-1 isoform
SEQ ID NO: 19
MIGLALLMLLGAAAAAVPRDVGKIVGGHECEPNSRPFMASLNYGYHFCGGV

LINDQWVLSVAHCWYNPYYMQVMLGEHDLRVFEGTEQLVKTNTIFWHELYD

YQTLDYDMMMIKLYHPVEVTQSVAPISLPTGPPDGGMLCSVSGWGNMAMGE

EVNLPTRLQCLDVPIVEPVACQASYPGMISPRMMCVGFMDGGRDVCNGDSG

SPLVCEGVLTGLVSWGRGCAEPNSPGVYVKVYEFLSWIQTTLDANP

Uncleaved Atlantic cod trypsin ZT-2 isoform
SEQ ID NO: 20
MIGLALLMLLGAAAAAVPRDVGKIVGGHECEPNSRPFMASLNYGYHFCGGV

LINDQWVLSVAHCWYNPYYMQVMLGEHDLRVFEGTEQLVKTNTIFWHELYD

YQTLDYDMMMIKLYHPVEVTQSVAPISLPTGPPDGGMLCSVSGWGNMAMGE

EVNLPTRLQCLDVPIVETVDCEAAYPGMISPRMVCAGYMDGGRDACNGDSG

SPLVCEGVLTGLVSWGQGCALPNYPGVYVKVYEYLSWIQTTLDANP

Uncleaved Atlantic cod trypsin ZT-3 isoform
SEQ ID NO: 21
MIGLALLMLLGAAAAVPREDGRIIGGQDCEPRSRPFMASLNYGYHFCGGVL

INDQWVLSVAHCWYNPYYMQVMLGEHDLRVFEGTEQLVKTNTIFWHELYDY

QTLDYDMMMIKLYHPVEVTQSVAPISLPTGPPDGGMLCSVSGWGNMAMGEE

VNLPTRLQCLDVPIVEPVACQASYPGMISPRMMCVGFMDGGRDVCNGDSGS

PLVCEGVLTGLVSWGRGCAEPNSPGVYVKVYEFLSWIQTTLDANP

Uncleaved Atlantic cod trypsin ZT-4 isoform
SEQ ID NO: 22
MIGLALLMLLGAAAAVPREDGRIIGGQDCEPRSRPFMASLNYGYHFCGGVL

INDQWVLSVAHCWYNPYYMQVMLGEHDLRVFEGTEQLVKTNTIFWHELYDY

QTLDYDMMMIKLYHPVEVTQSVAPISLPTGPPDGGMLCSVSGWGNMAMGEE

VNLPTRLQCLDVPIVETVDCEAAYPGMISPRMVCAGYMDGGRDACNGDSGS

PLVCEGVLTGLVSWGQGCALPNYPGVYVKVYEYLSWIQTTLDANP

Multiplex substrate profiling is used to analyze the substrate specificity of enzymes (proteinases) (O'Donoghue, Eroy-Reveles et al., 2012, *Nat Methods* 9: 1095-1100). Proteinases can cleave substrates at different amino residues within a peptide sequence demonstrating a difference in substrate specificity. Trypsins are specified by their preference in cleaving C-terminal to arginine or lysine residues. Unexpectedly, multiplex substrate profiling on trypsin ZT isoforms revealed that amino acids surrounding arginine or lysine in a substrate have a different effect on its cleavage compared to trypsin I. In short, trypsin ZT isoforms or trypsin I were incubated (5, 15 and 60 min.) with a library of peptides (124 defined peptides, 14-mer sequences, total of 1612 peptide bonds) with an extensive physiochemical diversity (O'Donoghue, Eroy-Reveles et al., 2012, *Nat Methods* 9: 1095-1100). After incubation, cleavage sites were identified by mass spectrometry analysis. The results are presented in the following examples and show that there are numerous cleavage sites unique to trypsin ZT compared trypsin I. Also, cleavage sites that showed preferential cleavage by trypsin ZT isoforms compared to trypsin I were identified. Further, the novel trypsin ZT isoforms have a different substrate specificity compared to a trypsin I, disclosed in WO 2000078332. These findings were unexpected. Based on the results from the multiplex substrate profiling analysis, a table containing numerical values based on standard scores (Z-score) ratio at the P4-P4' positions in the substrate was generated where the substrate specificity of trypsin ZT was compared to trypsin I. Positive values (Z-score) reflect a preference for the amino acid residue in a certain P position in favor of trypsin ZT isoforms compared to trypsin I.

Trypsin ZT isoforms have specific antimicrobial properties. Based on the values generated and presented in the examples, it can be seen that trypsin ZT isoforms are much better adapted in cleaving peptides containing several consecutive positively charged residues (arginine or lysine) compared to trypsin I. Those types of sequences (lysine and arginine rich amino acid sequence) are frequently found in viral proteins (Suzuki, Orba et al., 2010, *PLoS Pathog* 6: e1000801, Jiang, Cun et al., 2012, *J Virol* 86: 7256-7267, Gallaher and Garry, 2015, *Viruses* 7: 285-305).

Viroporins is a group of proteins that interact with plasma membranes modifying permeability and can promote the release of viral particles. Clustered lysine and/or arginine residues are important for the activity of viroporins. Based on the multiplex substrate profiling analysis, trypsin ZT isoforms can act as antiviral agents against RNA viruses as it can cleave these clustered basic amino acid residues. Viroporins have been described as present in a number of virus families, including the Flaviviridae, Picornaviridae, Retroviridae, Coronaviridae, Reoviridae and Paramyxoviridae (Royle, Dobson et al., 2015, *Viruses* 7: 5375-5387). Studies have shown that basic residues, lysine or arginine, in viroporins are a critical requirement for their function. The majority of viroporins have been identified in RNA viruses. Viruses that contain lysine and arginine rich viroporins that would be a target for trypsin ZT isoforms include human immunodeficiency virus (HIV), rotavirus, Ebola, Reston virus (RESTV), Lloviu virus (LLOV), Sudan virus (SUDV), Bundibugyo (BDBV), Tai Forest virus (TAFV) (Suzuki, Orba et al., 2010, *PLoS Pathog* 6: e1000801, Gallaher and Garry, 2015, *Viruses* 7: 285-305).

The viroporins are found in a wide variety of DNA and RNA viruses such as Paramecium bursaria chlorella virus 1, simian virus 40 (SV40), human polyoma JC (JCV), severe acute respiratory syndrome coronavirus (SARS-CoV) (Kang, Moroni et al., 2004, *Proc Natl Acad Sci USA* 101: 5318-5324, Liao, Tam et al., 2006, *Adv Exp Med Biol* 581: 199-202, Daniels, Sadowicz et al., 2007, *PLoS Pathog* 3: e98).

Highly basic viral proteins, termed agnoproteins, have recently have been identified from DNA viruses such as from the Polyomaviridae and Papillomaviridae family (Royle, Dobson et al., 2015, *Viruses* 7: 5375-5387). These proteins show a number of viroporin characteristics. Conserved sequences have been identified in agnoproteins that contain a number of clustered basic amino acid residues (Royle, Dobson et al., 2015, Viruses 7: 5375-5387). Based on the multiplex substrate profiling analysis, trypsin ZT isoforms can act as antiviral agents against DNA viruses as it can cleave these clustered basic amino acid residues (Royle, Dobson et al., 2015, *Viruses* 7: 5375-5387).

Many viruses and bacteria have developed mechanisms to gain cell entry using cell penetrating peptides or proteins (Milletti, 2012, *Drug Discov Today* 17: 850-860). The viruses include pestiviruses of the Flaviviridae family, herpes virus (HSV-1), human immunodeficiency virus (HIV-1, hepatitis B and human respiratory syncytial virus (RSV) (Elliott and O'Hare, 1997, *Cell* 88: 223-233, Oess and Hildt, 2000, *Gene Ther* 7: 750-758, Langedijk, 2002, *J Biol Chem* 277: 5308-5314, Langedijk, Olijhoek et al., 2005, *International Congress Series* 1277: 95-107, Lu, Tager et al., 2006, *Anal Biochem* 353: 7-14, Godet, Guergnon et al., 2010, *PLoS One* 5: e13760). Furthermore, these types of proteins have been found in bacteria such as *Mycobacterium tuberculosis* (Lu, Tager et al., 2006, *Anal Biochem* 353: 7-14). The cell penetrating peptides (CPP) have in common that they are rich in basic amino acid residues especially arginines (Milletti, 2012, *Drug Discov Today* 17: 850-860). Porins are outer membrane proteins that play a crucial role in bacterial pathogenicity and for protection and are for that reason useful targets for therapeutics (Galdiero, Falanga et al., 2012, *Curr Protein Pept Sci* 13: 843-854). These proteins often contain consecutive arginine amino acid residues. Based on the multiplex substrate profiling analysis trypsin ZT isoforms can act as antimicrobial agents against viruses and bacteria as it can cleave clustered basic amino acid residues.

Parasites depend on virulence determinants such as proteins containing arginine rich domains for example Toxoplasma gondii (Fentress, Steinfeldt et al., 2012, *Cell Microbiol* 14: 1921-1933). Multiplex substrate profiling analysis showed that trypsin ZT isoforms would be beneficial against parasites by acting against such proteins.

The Basic Local Alignment Search Tool (BLAST) was used to search for some of the unique and preferential amino acid sequences cleaved by trypsin ZT isoforms. The search results demonstrated that these types of sequences are found in many pathogens including viruses (e.g. from the Paramyxoviridae and Coronaviridae family of viruses), bacteria (e.g. *Haemophilus* genus) and parasites (e.g. *Plasmodium* genus). The Paramyxoviridae family includes viruses such as the respiratory syncytial virus (RSV) and human parainfluenza viruses and viruses that cause mumps and measles. The Coronaviridae family includes viruses that cause Severe Acute Respiratory Syndrome (SARS). The *Haemophilus* genus of bacteria includes *Haemophilus parainfluenzae* that is associated with endocarditis, meningitis, and bacteremia. The *Plasmodium* genus includes *Plasmodium falciparum* that causes malaria.

By the phrase "medical device" is meant, but not limited to, any instrument, apparatus, appliance, software, material or other article for the purpose of diagnosis, prevention, monitoring, treatment, or alleviation of disease, such as diagnosis, monitoring, treatment, alleviation of or compensation; for an injury or handicap, such as investigation, replacement or modification of the anatomy or of a physiological process; control of conception; including devices that do not achieve their principal intended action in or on the human body by pharmacological, immunological or metabolic means—but may be assisted in their function by such means.

The present invention relates to the novel trypsin ZT isoforms. The invention describes unpredicted and unique protein cleaving properties of trypsin ZT isoforms that make it valuable in medical applications. In particular, the invention relates to the novel Atlantic cod trypsin ZT isoforms, useful as pharmaceuticals, in medical devices, and cosmetics.

In one aspect of the invention, there is provided an isolated cod trypsin ZT isoform comprising an amino acid sequence according to SEQ ID NO:1, or an amino acid sequence with 80% sequence homology or more, thereof. Typically, such sequence homology is 85, 90, 95 or 99% homologous to the amino acid sequence of SEQ ID NO:1.

In one embodiment of this aspect there is provided an isolated cod trypsin ZT isoform, selected from trypsin ZT-1, comprising an amino acid sequence according to SEQ ID NO:2; trypsin ZT-2 comprising an amino acid sequence according to SEQ ID NO:3; trypsin ZT-3 comprising an amino acid sequence according to SEQ ID NO:4; and trypsin ZT-4, comprising an amino acid sequence according to SEQ ID NO:5, or an amino acid sequence with 80% sequence homology or more, thereof. Included are also amino acid sequences with 80% sequence homology or more, to amino acid sequences set out in SEQ ID NOS:2-5. Typically, such sequence homology is 85, 90, 95 or 99% homologous to the amino acid sequence of SEQ ID NOS: 2-5.

In one aspect of the invention, there is provided a composition comprising at least one cod trypsin ZT isoform according to the invention, together with suitable excipients and carriers. Said cod trypsin ZT isoform may be selected from cod trypsin ZT-1, comprising an amino acid sequence according to SEQ ID NO:2; cod trypsin ZT-2 comprising an amino acid sequence according to SEQ ID NO:3; cod trypsin ZT-3 comprising an amino acid sequence according to SEQ ID NO:4; and cod trypsin ZT-4 comprising an amino acid sequence according to SEQ ID NO:5. Included are also amino acid sequences with 80% sequence homology or more, to amino acid sequences set out in SEQ ID NOS:2-5. Typically, such sequence homology is 85, 90, 95 or 99% homologous to the amino acid sequence of SEQ ID NOS: 2-5.

Typically, said composition comprises said cod trypsin ZT isoforms present in admixture with other cod trypsins. Preferably, said cod trypsin ZT isoforms comprises at least 5% (w/w) of the total content of cod trypsins in said composition, such as at least 10, 15, 20, 25, 30, 35, 40, 45 or 50% or more (w/w) of the total content of cod trypsins in said composition.

Said composition is typically administered topically, as a lotion, a hydrogel, a mouth spray or a nasal spray. Said composition may further comprise a polyvalent alcohol, such as glycerol.

In one embodiment of this aspect, there is provided said composition for use in therapy.

In one embodiment of this aspect, there is provided said composition for use in treating or preventing a disease caused by a pathogenic organism selected from the group consisting of a virus, a bacterium, a fungus, a parasite and a protozoan.

In one embodiment of this aspect, there is provided said composition for use in treating or preventing a disease in the upper respiratory tract caused by pathogenic organisms such as viruses, bacteria and fungus.

In one embodiment of this aspect, there is provided said composition for use in treating or preventing pain, acute inflammation, chronic inflammation, arthritis, inflamed joints, bursitis, osteoarthritis, rheumatoid arthritis, juvenile rheumatoid arthritis, septic arthritis, fibromyalgia, systemic lupus erythematosus, phlebitis, tendinitis, rash, psoriasis, acne, eczema, facial seborrheic eczema, eczema of the hands, face or neck, foreskin infections, athlete's foot, fistulae infections, infected topical ulcers, navel infections in newborns, wrinkles, scars, kelloids, boils, warts and allergic itch, hemorrhoids, a fungal infection and an immunological disorder including an autoimmune disease.

In one embodiment of this aspect, there is provided said composition for use in the treatment of wound infections and wounds from burns.

In one embodiment of this aspect, there is provided said composition for use in removing dead or peeling skin from otherwise healthy skin.

In one embodiment of this aspect, there is provided said composition for cosmetic use. Said composition may further comprise an additional cosmetically active compound.

In one aspect of the invention, there is provided a method of treating disease, comprising administering a therapeutically effective amount of a composition according to the present invention, to a patient in need thereof.

In one embodiment of this aspect, said disease is caused by a pathogenic organism selected from the group consisting of a virus, a bacterium, a fungus, a parasite and a protozoan In one embodiment of this aspect, said disease is a disease in the upper respiratory tract caused by pathogenic organisms such as viruses and bacteria.

In one embodiment of this aspect, said disease is selected from pain, acute inflammation, chronic inflammation, arthritis, inflamed joints, bursitis, osteoarthritis, rheumatoid arthritis, juvenile rheumatoid arthritis, septic arthritis, fibromyalgia, systemic lupus erythematosus, phlebitis, tendinitis, rash, psoriasis, acne, eczema, facial seborrheic eczema, eczema of the hands, face or neck, foreskin infections, athlete's foot, fistulae infections, infected topical ulcers, navel infections in newborns, wrinkles, scars, kelloids, boils, warts and allergic itch, hemorrhoids, a fungal infection and an immunological disorder including an autoimmune disease.

In one embodiment of this aspect, said disease is wound infections or wounds from burns.

In one aspect of the invention, there is provided an isolated cod trypsin ZT isoform, selected from full length trypsin ZT-1, comprising an amino acid sequence according to SEQ ID NO:19; full length trypsin ZT-2 comprising an amino acid sequence according to SEQ ID NO:20; full length trypsin ZT-3 comprising an amino acid sequence according to SEQ ID NO:21; and full length trypsin ZT-4, comprising an amino acid sequence according to SEQ ID NO:22.

In one aspect of the invention, there is provided a method of preparing cod trypsin ZT isoforms comprising an amino acid sequence according to any one of SEQ ID NO:2 to SEQ ID NO:5, comprising
(i) extracting trypsin ZT from cod viscera,
(ii) applying the extract to at least one or more chromatography steps, including an affinity chromatography step using a p-aminobenzamidine affinity ligand, and
(iii) desorbing and eluting cod trypsin ZT isoforms bound to the p-aminobenzamidine affinity ligand.

In one embodiment of this aspect, said method further comprises at least one step using an anionic exchange resin after said affinity chromatography step (ii).

In one embodiment of this aspect, said cod trypsin ZT isoforms are selected from trypsin ZT-1, comprising an amino acid sequence according to SEQ ID NO:2; trypsin ZT-2 comprising an amino acid sequence according to SEQ ID NO:3; trypsin ZT-3 comprising an amino acid sequence according to SEQ ID NO:4; and trypsin ZT-4 comprising an amino acid sequence according to SEQ ID NO:5, or a mixture thereof.

Cod viscera is typically used to purify and isolate trypsin ZT isoforms. The inventors have identified novel methods described below, useful for a commercial scale production of trypsin ZT isoforms. Extraction is conducted at a pH of 6-8 at a temperature below 10° C. Cod viscera is mixed with water at a ratio (w/w) of 1:6 to 1:20. The extract is separated from the leftover offal and further clarified by sedimentation and filtration. This is followed by microfiltration and ultrafiltration resulting a solution containing trypsin ZT isoforms that is used for chromatography separation that may include several steps.

An affinity chromatography is conducted, preferably by amino benzamidine affinity chromatography, to purify trypsin ZT isoforms. Trypsin ZT isoforms can then be further purified with anion exchange chromatography.

One method of application of trypsin ZT isoforms or mixtures of purified cod trypsins containing trypsin ZT isoforms, is in a preparation of hydrogel or lotion and water containing 0 to 90% (vol/vol) of a polyvalent alcohol (polyol) such as glycerol. A suitable concentration of trypsin ZT isoforms constitutes at least 1 to 100 protein concentration ratio to other trypsin forms, preferably 5%, or higher (w/w) of the total content of cod trypsins. The trypsin activity is 0.1 to 10,000 enzyme units of activity for CBZ-Gly-Pro-Arg-pNA (carbobenzoxy Gly-Pro-Arg-para nitroanilide) per 100 milliliters of the final hydrogel/lotion preparation.

The invention further provides (a) methods relating to certain conditions using effective amounts of the purified trypsin ZT isoforms described above, (b) compositions or substances for use in such methods, (c) pharmaceutical or medical device compositions containing effective amounts of trypsin ZT isoforms for use in such methods, and (d) uses of the enzyme or enzyme composition for manufacturing a medicament (pharmaceutical and medical devices) for use in such methods.

The methods are inter alia for:

treating or preventing pathogenic disease caused by viruses, bacteria and fungi that for example occur in the upper respiratory tract, lower respiratory tract and in lungs;

treating or prophylactically preventing dermatological conditions such as e.g. acne, rash, psoriasis or eczema, including facial seborrheic eczema or eczema of the hands, face, scalp or neck, hemorrhoids and the like, where preferably the amount of the trypsin ZT isoforms and other trypsins administered is a dermatological condition treating or preventing effective amount;

treating lung diseases where trypsin ZT isoforms with or without other trypsins are used for example in pressurized metered dose high efficiency inhaler in an effective dose for treatment;

treating or prophylactically preventing wound infection and debriding wounds (by applying to the wound a microbial infection-preventing effective amount of trypsin ZT isoforms with or without other trypsins or by enhancing the healing of wounds by administering a microbe inhibiting effective amount of trypsin ZT isoforms with or without other trypsins, when treated the wound can be substantially freed of necrotic tissue; treating burns, where preferably the amount of trypsin ZT isoforms with or without other trypsins administered in a sufficient amount to promote healing;

treating sunburns, where preferably the amount of trypsin ZT isoforms with or without other trypsins administered in a sufficient amount to promote healing;

treating radiation burns, where preferably the amount of trypsin ZT isoforms with or without other trypsins administered in a sufficient amount to promote healing;

removing dead or peeling skin from otherwise healthy skin to improve the skin's appearance, where preferably the amount of trypsin ZT isoforms with or without other trypsins is administered in a dead skin removing effective amount;

treating cracked heels, where preferably the amount of trypsin ZT isoforms with or without other trypsins is administered in a sufficient amount for effective treatment;

for management of irritated skin, such as dry patches, itching, redness and blemishes, where preferably the amount of trypsin ZT isoforms with or without other trypsins is administered in a sufficient amount for effective treatment;

treating or prophylactically preventing cystic fibrosis, cancer, e.g. by administering a tumor treating effective amount or a tumor metastasis preventing or inhibiting amount of trypsin ZT isoforms, atherosclerosis, asthma, septic shock, toxic shock syndrome, tissue adhesions such as tendon-sheath, abdominal post-surgical or joint adhesions, reperfusion injury, malaria, immune disorder such as an autoimmune disease, apoptosis, colitis and enteritis, such as Crohn's disease, where preferably the amount of trypsin ZT isoforms and related peptidases administered are effective;

treating or prophylactically preventing a microbial infection, e.g. a viral infection such as a rhinovirus (RV), respiratory syncytial virus (RSV), influenza, herpes virus infection (e.g. HSV-1, HSV-2, herpes zoster or genital herpes infection), HIV, hepatitis, coronavirus, cytomegalovirus or papilloma virus infection; an infection causing a gastrointestinal disease such as ulcer or diarrhea; a fungal infection such as systemic, skin, oral, vaginal or esophageal fungal infection, including e.g. yeast infection, including a fungal nail infection and Candida infections; microbial infections of the eye, preferably treated with ocular administrations; bacterial infections including infection by *Helicobacter pylori, Staphylococcus* spp., Methicillin-resistant *Staphylococcus aureus* (MRSA), *Streptococcus pneumonia, Haemophilus influenza, Streptococcus mitis, Streptococcus* spp., *Klebsiella* spp., *Pseudomonas* spp., *Neisseria gonorrheae, Haemophilus* spp., *Chlamydia* spp., *syphilis* and *E. coli* infections and bacterial infections causing chancroid; opportunistic microbial infections in immunocompromised patients where preferably the administered amount of the cod trypsins is a microbial infection-treating or -preventing effective amount or has inhibitory activity against cell-cell or cell-virus adhesion;

treating or prophylactically preventing an indication selected from the group consisting of pain, inflammation, acute or chronic inflammation, arthritis, inflamed joints, bursitis, osteoarthritis, rheumatoid arthritis, juvenile rheumatoid arthritis, septic arthritis, fibromyalgia, systemic lupus erythematosus and phlebitis where preferably the amount is treating or preventing effective amount;

removing dental plaque, where preferably the amount of trypsin ZT isoforms with or without other trypsins is administered in a dental plaque removing effective amount; and lysing blood clots, where preferably the amount of trypsin ZT isoforms is a clot lysing effective amount.

The method comprises administering a composition comprising the trypsin ZT isoforms as described above.

The invention provides topical cosmetic and medical compositions comprising trypsin ZT isoforms described above; and gel, cream or suppository composition.

The invention further provides a method of inhibiting or prophylactically preventing the transmission of a pathogenic microbe by administering trypsin ZT isoforms with or without other trypsins. Preferably, trypsin ZT with or without other trypsins is applied to the portion of the body that comprises the primary transmission entryway for the microbe in question. In one embodiment, a spray, ointment or wash is applied to a body orifice involved in sexual activity, for instance, to prevent HIV or hepatitis transmission. In another embodiment, trypsin ZT isoforms or related peptidases is applied to the upper airways, for example, via an aerosol, to inhibit or prevent the transmission of a common cold virus, such as a rhinovirus or a coronavirus.

The method of extra-corporeally treating a tissue, body fluid or composition of cells to remove cell adhesion components reduces the immune rejection of tissue, body fluid or composition of cells that is transplanted from one individual to another. In another aspect, such treatments remove or inactivate the cell adhesion components found in the treated tissue, body fluid or composition of cells involved in a microbial infection.

In treating or prophylactically preventing septic shock or toxic shock syndrome by administering trypsin ZT isoforms or related peptidases, appropriate routes of administration include systemic administration. For vaginal infections associated with shock, vaginal flushes, creams, gels or suppositories may be used as a method of administration. In treating or prophylactically preventing pain, inflammation, acute or chronic inflammation, arthritis, inflamed joints, bursitis, osteoarthritis, rheumatoid arthritis, juvenile rheumatoid arthritis, septic arthritis, fibromyalgia, systemic lupus erythematosus, phlebitis by administering trypsin ZT isoforms or related peptidases, appropriate routes of administration would include without limitation creams, gels or suppositories, in particular but not limited to hydrogels containing glycerol or other polyols.

In treating or prophylactically preventing rash, psoriasis, acne, eczema, including facial seborrheic eczema or eczema of the hands, face, scalp or neck, foreskin infections, athlete's foot, fistulae infections, infected topical ulcers, navel infections in newborns, wrinkles, scars and kelloids, boils, warts and allergic itch, hemorrhoids and the like, wounds, wound infections, wounds from burns, removing dead or peeling skin from otherwise healthy skin to improve the skin's appearance, a fungal infection such as systemic, skin, oral, vaginal or esophageal fungal, including for example, yeast infection, including a fungal nail infection and Candida infections and immune disorders including autoimmune diseases by administering trypsin ZT isoforms with or without other trypsins, appropriate routes of administration would include creams, gels or suppositories, in particular but not limited to hydrogels containing glycerol or other polyols.

The above objectives are achieved by using a composition containing an effective amount of trypsin ZT isoforms with or without other trypsins which is capable of relieving the pain, inflammation, arthritis, swelling, edema, psoriasis eczema, dermatitis, rash and/or other symptoms of the diseases mentioned in the introductory part. Trypsin ZT isoforms can be obtained at a high yield and in a relatively simple manner from cod viscera. It has been found that trypsin ZT isoforms can be purified on a commercial scale in a relatively straightforward manner with reasonable yields. Trypsin ZT isoforms without or along with other Atlantic serine proteases can be used for the purpose of the invention.

Trypsin ZT isoforms presented in the present disclosure can be desorbed from the affinity matrix by applying conditions that will destabilize the interaction between the enzyme and the affinity ligand. Such conditions include high salt followed by low pH, preferably in 30% or more glycerol. The column eluent is allowed to flow into a neutralizing buffer to stabilize the cod trypsin after the acid elution step. Trypsin ZT isoforms can then be further purified using anion exchange and eluted with increasing salt concentration. By these methods trypsin ZT isoforms with a purity in excess of about 90% can be isolated. The cod trypsin fraction thus obtained contains 2-3 major isoforms as manifested by SDS electrophoresis, which yields two bands and MALDI-TOF mass spectrometry analysis. The molecular mass of trypsin ZT isoforms is about 25 kDa, whereas the calculated isoelectric point is 4.35-4.49 depending on the isoform.

Trypsin ZT isoforms with or without other trypsins in specific formulations can be used as a pharmaceutical, in medical devices (such as chemical formulations) or in cosmetics depending on intended use. Trypsin ZT isoforms (with or without other trypsins) of the invention are administered topically, orally, rectally, vaginally, by instillation (for instance into the urinary tract or into fistulas), by the pulmonary route e.g. by use of an aerosol (for example by using a pressurized metered-dose inhaler (pMDI)), by application of drops to the eye, or systemically, such as parenterally, including, for example, intramuscularly, subcutaneously, intraperitoneally, intraarterially or intravenously. Trypsin ZT isoforms are administered in solution or combined with a pharmaceutically acceptable carrier or excipient according to standard pharmaceutical practice. For the oral mode of administration, trypsin ZT isoforms are used in the form of tablets, capsules, lozenges, chewing gum, troches, powders, syrups, elixirs, aqueous solutions and suspensions, and the like. For parenteral administration, sterile solutions of trypsin ZT isoforms are usually prepared, and the pH values of the solutions are suitably adjusted and buffered. For intravenous use, the total concentration of solutes should be controlled to render the preparation isotonic. For ocular administration, ointments or droppable liquids may be delivered by ocular delivery systems known to the art such as applicators or eye droppers. For pulmonary administration, diluents and/or carriers will be selected to be appropriate to allow the formation of an aerosol. For topical administrations, trypsin ZT isoforms are typically administered in a hydrogel, containing 0 to 85% glycerol, such as about 20% to 30% glycerol and possibly up to 85% glycerol.

For topical treatments, a suitable dose of trypsin ZT isoforms with or without other trypsins per application ranges from about 0.01 µg/cm$^2$ to about 1 mg/cm$^2$, preferably from about 0.1 µg/cm$^2$ to about 0.01 mg/cm$^2$ (using e.g. about 0.01 mg/ml enzyme gel). For systematic treatments, dosages will generally be selected to maintain a serum level of trypsin ZT isoforms with or without other trypsins between about 0.1 mg/100 ml and about 100 mg/100 ml, preferably between about 0.5 mg/100 ml and about 2.0 mg/100 ml. In an alternative measure of preferred systematic administration amounts, preferably from about 0.1 mg/kg to about 10 mg/kg, more preferably about 1 mg/kg, will be used. For vaginal and urinary tract treatments, suitable flushing/instillation solutions of trypsin ZT isoforms will generally have concentrations from about 1 µg/ml to about 15 mg/ml, preferably from about 100 µg/ml to about 3 mg/ml. For all treatments, the enzyme composition will generally be applied from about 1 to about 10 times per day, preferably from about 2 to about 5 times per day. These values, of course, will vary with a number of factors including the type and severity of the disease, and the age, weight and medical condition of the patient, as will be recognized by those of ordinary skill in the medical arts. It is believed that substantially higher doses can be used without substantial adverse effect.

For wound healing, trypsin ZT isoforms with or without other trypsins are preferably applied more often than simply at the time at which the wound is first dressed. Preferably, trypsin ZT isoforms are applied at least about every time the wound dressing is changed. Trypsin ZT isoforms can also be applied at least about every other day, more preferably, every day, or few times per day. For dermatological situations such as eczema, psoriasis and the like, a trypsin ZT isoform (with or without other trypsins) hydrogel is preferably applied every day, more preferably twice per day. For acute or chronic inflammation, arthritis, inflamed joints, bursitis, osteoarthritis, and the like, trypsin ZT isoforms are preferably applied every day more preferably twice every day.

Numerous methods for determining percent homology of proteins are known in the art. Percent Identity was calculated using ClustalW2 (version Clustal2.1) when making sequence comparisons (EMBL-EBI website http://www.ebi.ac.uk/Tools/msa/clustalw2/date 4th of May 2015).

The invention will now be described by a number of non-limiting examples.

Example 1

Preparation of a Mixture of Proteases from Cod

About 100 kg of frozen Atlantic cod viscera were thawed and added to a four-fold volume of cold potable water in an extraction tank and the pH adjusted to around pH 6 with sodium hydroxide solution. The mixture was stirred for about 10 hours at 0 to 5° C. After a brief period of crude sedimentation (about 30 minutes) the aqueous extract was run off the remaining insoluble viscera with a pump and collected in a sedimentation tank. The aqueous extract was allowed to stand in the cooled sedimentation tank to sediment for about 40 to 80 hours. The supernatant was decanted from the supernatant tank to a holding tank using a pump. The supernatant was concentrated 10 to 20-fold by ultrafiltration and diafiltered to an acceptable level of ionic strength with conductivity below about 2.5 mS/cm. About 10-15 liters of ultrafiltered and diafiltered protein concentrate was obtained.

Example 2

Purification of Cod Trypsin ZT Isoforms from Concentrated Cod Viscera Extract

About 12 liters of ultrafiltered and diafiltered concentrate as obtained in Example 1 was applied to a continuous, connected series of about 1 liter packed chromatography columns, the first containing a carboxymethyl (CM) fast flow cation exchange resin (GE healthcare) and the second one a p-aminobenzamidine affinity ligand coupled to a sepharose resin (GE healthcare). The CM and p-aminobenzamidine columns were pre-equilibrated with about 10 column volumes of 25 mM Tris buffer of pH 7.8, containing 2.5 mM calcium chloride (buffer A). The concentrate was pumped onto the CM and p-aminobenzamidine columns at a flow rate of about 100 ml per minute. When the application of the concentrated solution onto the columns was completed, residual material was washed off the continuous column system with about 8 liters of buffer A. After this wash was completed, the p-aminobenzamidine affinity column was disconnected from the CM column and washed with about 5 column volumes of a high salt solution of 25 mM Tris buffer pH 7.5 containing 0.5 M NaCl and 2.5 mM calcium chloride. The cod trypsins were then desorbed from the affinity ligand and eluted off the column with an acid solution of 25 mM acetic acid pH 3.2 containing 10 mM calcium chloride and 30% glycerol.

Figure 2:
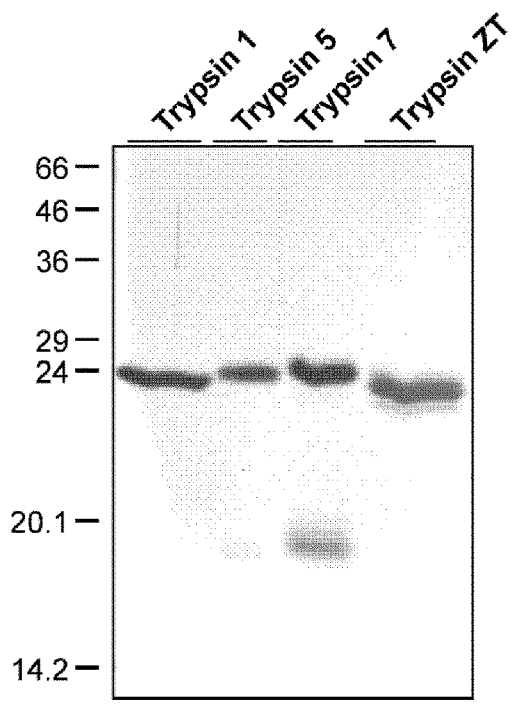
FIG. 2 shows SDS-PAGE of cod trypsin ZT isoforms. SDS-PAGE analysis of anion exchange chromatography peak labeled trypsin ZT from FIG. 1. Trypsin 1, trypsin 5 and trypsin 7 are purified and isolated cod trypsin X isoforms. Cod trypsin X is closely related to cod trypsin I, differ by about eight amino acid residues. The proteins were resolved by SDS-PAGE and the gel silver stained. The bars and numbers on the left show the migration and molecular weight in kDa of standard proteins (Dalton Mark VII-L) separated on the gel.
Figure 3:
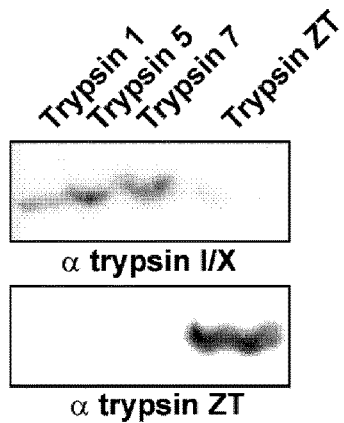
FIG. 3 shows Western blot analysis of cod trypsin X (trypsin 1, trypsin 5 and trypsin 7) and trypsin ZT isoforms. Cod trypsin X and trypsin ZT isoforms were subjected to SDS-PAGE. Following transfer, samples were immunoblotted with trypsin I/X (top panel) and trypsin ZT isoform (bottom panel) reacting antibodies. This shows that trypsin ZT isoforms were separated from trypsin I/X using anion exchange. As can be seen in FIG. 3, the polyclonal antibody that reacts against trypsin ZT isoforms does not cross-react with trypsin I/X and the peptide antibody raised against trypsin I/X does not cross-react with trypsin ZT isoforms.

The purified cod trypsin ZT isoform-containing preparation was homogeneous by SDS PAGE electrophoresis. The purified preparation was filter-sterilized through a 0.22 micron filter and stored frozen at about −20° C. The cod trypsin ZT isoform-containing preparation was filter-sterilized through a 0.22 micron filter and stored frozen at about −20° C. The cod trypsin ZT isoform-containing preparation was applied to an anion exchange chromatography column (MonoQ) and proteins eluted with a salt gradient (FIG. 1). The column was equilibrated with a buffer (20 mM Tris, 10 mM $CaCl_2$, pH 8.0), and the enzymes were eluted with a linear 0-150 mM NaCl gradient in 40 column volumes, linear 150-620 mM NaCl in 6 column volumes, 620-850 mM NaCl in 10 column volumes at a flow rate of 1 mL/min. The proteins in the peak labeled trypsin ZT from FIG. 1 were subjected to SDS-PAGE analysis (FIG. 2). The protein band on the gel from the trypsin ZT peak was excised from the gel and analyzed using Matrix-Assisted Laser Desorption/Ionization Time-of-Flight Mass Spectrometry (MALDI-TOF MS). The mass spectrometry (MS) analysis revealed identity to trypsin ZT-1, trypsin ZT-2, trypsin ZT-3 and trypsin ZT-4 (Table 1 and Table 2). Antibodies against trypsin I and trypsin X were prepared in rabbits against a peptide (($NH_2$—) CVLSGWVRDTMA (—COOH)) (SEQ ID NO: 23) corresponding to residues 228-239 at the extreme C terminus of cod trypsin I and cod trypsin X. The antibodies were affinity purified from rabbit serum using the peptide coupled to a gel bead support. Polyclonal antibodies against trypsin ZT isoforms were made in mouse ascitic fluid as described in Overkamp et al. (Overkamp, Mohammed-Ali et al., 1988, *J Immunoassay* 9: 51-68). A purified form of recombinant trypsin ZT-4 was injected intraperitoneally (i.p.) into Balb/C2 mice. The mice were sacrificed on day 34 and ascitic fluid collected. The respective antibodies were used in Western blot analysis. Western blot analysis was performed on the proteins in the peak labeled trypsin ZT from FIG. 1 (FIG. 3). Trypsin ZT isoform antibody reacted against the proteins from the peak labeled trypsin ZT whereas an antibody against trypsin I and trypsin X did not (FIG. 3).

Table 1 shows peptide masses obtained from MS analysis on protein band from SDS-PAGE gel in FIG. 2 (non guanidilated sample), see column 1 Mr (expt). Mr stands for relative molecular mass in Da. Columns 2, 3 and 4 show the calculated values (for masses matching to masses in column 1) from an in silico trypsin digest of the amino acid sequences trypsin ZT-1, trypsin ZT-2, trypsin ZT-3 and trypsin ZT-4. Column 5 shows the sequence of the peptide that give the mass value from the in silico digest. Column 6 shows modifications of the different peptides based on the in silico digest.

TABLE 1

| Mr (expt) | Trypsin ZT-4 | Trypsin ZT-3 | Trypsin ZT-2 | Trypsin ZT-1 | Sequence | Modifications |
|---|---|---|---|---|---|---|
| 842, 4077 | | | | | | |
| 1045, 4976 | | | | | | |
| 1082, 5603 | | | | | | |
| 1144, 4826 | 1144, 5415 | 1144, 5415 | | | (R)IIGGQDCEPR(S) | Carbamidomethyl (C) |
| 1149, 5283 | 1149, 6150 | 1149, 6150 | 1149, 6150 | 1149, 6150 | (R)VFEGTEQLVK(T) | |
| 1212, 4511 | | | | | | |
| 1216, 4408 | 1216, 4908 | | 1216, 4908 | | (R)MVCAGYMDGGR(D) | Carbamidomethyl (C) |
| 1260, 4492 | | 1260, 4992 | | 1260, 4992 | (R)MMCVGFMDGGR(D) | Carbamidomethyl (C) |
| 1262, 4221 | 1262, 4962 | | 1262, 4962 | | (R)MVCAGYMDGGR(D) | 2 Oxidation (M) Propionamide (C) |
| 1276, 4272 | | 1276, 4941 | | 1276, 4941 | (R)MMCVGFMDGGR(D) | Carbamidomethyl (C) Oxidation (M) |
| 1320, 5165 | | 1320, 6253 | | 1320, 6253 | (R)GCAEPNSPGVYVK(V) | |
| 1354, 5907 | | | | | | |
| 1377, 5624 | | 1377, 6467 | | 1377, 6467 | (R)GCAEPNSPGVYVK(V) | Carbamidomethyl (C) |
| 1493, 5870 | | | | | | |
| 1638, 7873 | | | | | | |
| 1707, 6807 | | | | | | |
| 1839, 8099 | | | | | | |
| 1994, 9057 | | | | | | |

TABLE 1-continued

| Mr (expt) | Trypsin ZT-4 | Trypsin ZT-3 | Trypsin ZT-2 | Trypsin ZT-1 | Sequence | Modifications |
|---|---|---|---|---|---|---|
| 2800, 2263 | | 2800, 3831 | | 2800, 3831 | (R)LQCLDVPIVEPVAC QASYPGMISPR(M) | 2 Carbamidomethyl (C) |
| 2814, 2398 | | 2814, 3987 | | 2814, 3987 | (R)LQCLDVPIVEPVAC QASYPGMISPR(M) | Carbamidomethyl (C) Propionamide (C) |
| 2830, 2763 | | 2830, 3936 | | 2830, 3936 | (R)LQCLDVPIVEPVAC QASYPGMISPR(M) | Carboxymethyl (C) Oxidation (M) Propionamide (C) |
| 2847, 3361 | 2847, 3725 | | 2847, 3725 | | (R)LQCLDVPIVETVDC EAAYPGMISPR(M) | Carbamidomethyl (C) Propionamide (C) |

The sequences in Table 1 are as follows:

| Seq ID NO | Amino acid sequence |
|---|---|
| SEQ ID NO 6 | IIGGQDCEPR |
| SEQ ID NO 7 | VFEGTEQLVK |
| SEQ ID NO 8 | LQCLDVPIVEPVACQASYPGMISPR |
| SEQ ID NO 8 | LQCLDVPIVEPVACQASYPGMISPR |
| SEQ ID NO 8 | LQCLDVPIVEPVACQASYPGMISPR |
| SEQ ID NO 9 | LQCLDVPIVETVDCEAAYPGMISPR |
| SEQ ID NO 10 | MVCAGYMDGGR |
| SEQ ID NO 11 | MMCVGFMDGGR |
| SEQ ID NO 10 | MVCAGYMDGGR |
| SEQ ID NO 11 | MMCVGFMDGGR |
| SEQ ID NO 12 | GCAEPNSPGVYVK |
| SEQ ID NO 12 | GCAEPNSPGVYVK |

Table 2 shows peptide masses obtained from MS analysis on protein band from SDS-PAGE gel in FIG. 2 (guanidilated sample), see column 1 Mr (expt). Mr stands for relative molecular mass in Da. Columns 2, 3 and 4 show the calculated values (for masses matching to masses in column 1) from an in silico trypsin digest of the amino acid sequences of trypsin ZT-1, trypsin ZT-2, trypsin ZT-3 and trypsin ZT-4. Column 5 shows the sequence of the peptide that give the mass value from the in silico digest. Column 6 shows modifications of the different peptides based on the in silico digest.

TABLE 2

| Mr (expt) | Trypsin ZT-4 | Trypsin ZT-3 | Trypsin ZT-2 | Trypsin ZT-1 | Sequence | Modifications |
|---|---|---|---|---|---|---|
| 781, 5661 | | | | | | |
| 842, 4931 | | | | | | |
| 1144, 5651 | 1144, 5415 | 1144, 5415 | | | (R)IIGGQDCEPR(S) | Carbamidomethyl (C) |
| 1173, 6305 | | | | | | |
| 1191, 6567 | 1191, 6368 | 1191, 6368 | 1191, 6368 | 1191, 6368 | (R)VFEGTEQLVK(T) | Guanidinyl (K) |
| 1210, 5861 | | | | | | |
| 1212, 5237 | | | | | | |
| 1216, 5105 | 1216, 4908 | | 1216, 4908 | | (R)MVCAGYMDGGR(D) | Carbamidomethyl (C) |
| 1222, 6291 | | | | | | |
| 1260, 5201 | | 1260, 4992 | | 1260, 4992 | (R)MMCVGFMDGGR(D) | Carbamidomethyl (C) |
| 1270, 6331 | | | | | | |
| 1276, 5112 | | 1276, 4941 | | 1276, 4941 | (R)MMCVGFMDGGR(D) | Carbamidomethyl (C) Oxidation (M) |
| 1638, 8623 | | | | | | |
| 1993, 9786 | | | | | | |

TABLE 2-continued

| Mr (expt) | Trypsin ZT-4 | Trypsin ZT-3 | Trypsin ZT-2 | Trypsin ZT-1 | Sequence | Modifications |
|---|---|---|---|---|---|---|
| 2635, 2760 |  | 2635, 2127 |  | 2635, 2127 | (R)DVCNGDSGSPLVC EGVLTGLVSWGR(G) | Carbamidomethyl (C) Carboxymethyl (C) |
| 2649, 2755 |  | 2649, 2283 |  | 2649, 2283 | (R)DVCNGDSGSPLVC EGVLTGLVSWGR(G) | Carboxymethyl (C) Propionamide (C) |
| 2752, 4779 |  |  |  |  |  |  |
| 2762, 6478 |  |  |  |  |  |  |
| 2766, 5037 |  |  |  |  |  |  |
| 2776, 6052 | 2776, 3354 |  | 2776, 3354 |  | (R)LQCLDVPIVETVD CEAAYPGMISPR(M) |  |
| 2800, 4952 |  | 2800, 3831 |  | 2800, 3831 | (R)LQCLDVPIVEPVA CQASYPGMISPR(M) | 2 Carbamidomethyl (C) |
| 2814, 5098 |  | 2814, 3987 |  | 2814, 3987 | (R)LQCLDVPIVEPVA CQASYPGMISPR(M) | Carbamidomethyl (C) Propionamide (C) |
| 2830, 5112 |  | 2830, 3936 |  | 2830, 3936 | (R)LQCLDVPIVEPV ACQASYPGMISPR(M) | Carboxymethyl Oxidation Propionamide |
| 2833, 4913 | 2833, 3569 |  | 2833, 3569 |  | (R)LQCLDVPIVETV DCEAAYPGMISPR(M) | 2 Carbamidomethyl |
| 2847, 5160 | 2847, 3725 |  | 2847, 3725 |  | (R)LQCLDVPIVETV DCEAAYPGMISPR(M) | Carbamidomethyl (C) Propionamide |

The sequences in Table 2 are as follows:

| Seq ID No | Amino acid sequence |
|---|---|
| SEQ ID NO 6 | IIGGQDCEPR |
| SEQ ID NO 7 | VFEGTEQLVK |
| SEQ ID NO 9 | LQCLDVPIVETVDCEAAYPGMISPR |
| SEQ ID NO 8 | LQCLDVPIVEPVACQASYPGMISPR |
| SEQ ID NO 8 | LQCLDVPIVEPVACQASYPGMISPR |
| SEQ ID NO 8 | LQCLDVPIVEPVACQASYPGMISPR |
| SEQ ID NO 9 | LQCLDVPIVETVDCEAAYPGMISPR |
| SEQ ID NO 9 | LQCLDVPIVETVDCEAAYPGMISPR |
| SEQ ID NO 10 | MVCAGYMDGGR |
| SEQ ID NO 11 | MMCVGFMDGGR |
| SEQ ID NO 11 | MMCVGFMDGGR |
| SEQ ID NO 13 | DVCNGDSGSPLVCEGVLTGLVSWGR |
| SEQ ID NO 13 | DVCNGDSGSPLVCEGVLTGLVSWGR |

Example 3

Multiplex Substrate Profiling on Trypsin ZT Isoforms

Multiplex substrate profiling was used to analyze the substrate specificity of enzymes (proteinases) (O'Donoghue, Eroy-Reveles et al., 2012, Nat Methods 9: 1095-1100). Proteinases can cleave substrates at different amino residues within a peptide sequence demonstrating a difference in substrate specificity. Trypsins are specified by their preference in cleaving C-terminal to arginine or lysine residues.

Enzyme Isoforms

The cod trypsin isoenzymes were separated by applying benzamidine purified cod trypsin to a MonoQ HR 5/5 ion exchange column. For isolation of trypsin I, the column was equilibrated with 20 mM Tris, 5 mM ethanolamine, 10 mM $CaCl_2$, pH 9.1, and the enzymes were eluted with a linear 0-200 mM NaCl gradient in 80 column volumes, linear 200-1000 mM NaCl gradient in 10 column volumes at a flow rate of 1 mL/min. The sample pH was adjusted to pH 9.1 with 1 M NaOH before application.

For isolation of trypsin ZT isoforms, the column was equilibrated with 25 mM Tris, 25 mM $CaCl_2$, 15% (vol/vol) glycerol, pH 7.5, and the enzymes were eluted with a linear 0-150 mM NaCl gradient in 5 column volumes, linear 150-550 mM NaCl gradient in 20 column volumes, linear 500-1000 mM NaCl gradient in 1 column volume at a flow rate of 1 mL/min.

The composition of both enzyme samples (trypsin ZT and trypsin I) was adjusted so the final concentration of Tris was 60 mM, $CaCl_2$ 30 mM and glycerol 15% (vol/vol) with a pH of 8.5.

Multiplex Substrate Profiling Analysis

The purified trypsin ZT isoforms or trypsin I were incubated (5, 15 and 60 min.) with a library of peptides (124 defined peptides, 14-mer sequences, total of 1612 peptide bonds) with an extensive physiochemical diversity as described in O'Donoghue, Eroy-Reveles et al. (O'Donoghue, Eroy-Reveles et al., 2012, Nat Methods 9: 1095-1100). After incubation, cleavage sites were identified by mass spectrometry analysis (O'Donoghue, Eroy-Reveles et al., 2012, Nat Methods 9: 1095-1100).

Results

Figure 4:
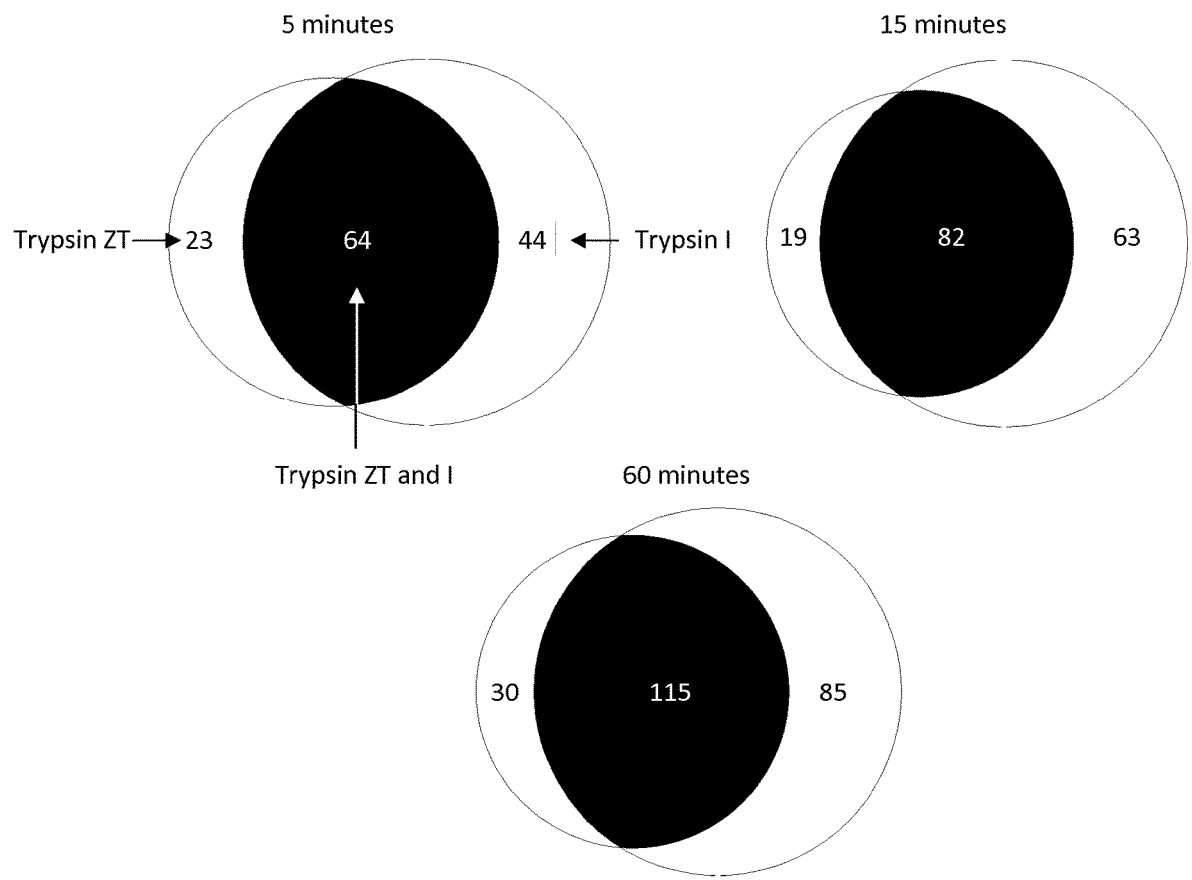
FIG. 4 shows a Venn diagram illustrating shared and unique cleavages generated by trypsin ZT and trypsin I at three different time points in a multiplex substrate profiling analysis. Number of shared (black) and unique cleavage sites by trypsin ZT (white on the left) and trypsin I (white on the right) after incubation for 5 min. (A), 15 min. (B) and 60 min (C). The figure shows that at all time points there are shared cleavage sites and unique cleavage sites for trypsin ZT and trypsin I in the 124 defined peptides (each containing 14 amino acid residues) within the library. The data demonstrates that the substrate specificity of trypsin ZT is different from that of trypsin I.

The multiplex substrate profiling analysis unexpectedly showed that there are numerous cleavage sites unique to trypsin ZT isoforms compared trypsin I, disclosed in WO 2000078332 (FIG. 4 and Table 4). Also, cleavage sites that showed preferential cleavage by trypsin ZT isoforms compared to trypsin I were identified (Table 4). Based on the results from the multiplex substrate profiling analysis, a table containing numerical values based on standard scores (Z-score) ratio at the P4-P4' positions in the substrate was generated where the substrate specificity of trypsin ZT was compared to trypsin I (Table 3). Positive values (Z-score) reflect a preference for the amino acid residue in a certain P position in favor of trypsin ZT isoforms compared to trypsin I. Unexpectedly, multiplex substrate profiling on trypsin ZT isoforms revealed that amino acids surrounding arginine or lysine in a substrate have a different effect on its cleavage compared to trypsin I.

Table 3 shows numerical values based on standard scores (Z-score) ratio at the P4-P4' positions in the substrate comparing the substrate specificity of trypsin ZT and trypsin I after incubation for 5, 15 and 60 min. Amino acid residues in a substrate undergoing cleavage were designated P1, P2, P3, P4 in the N-terminal direction from the cleaved bond (Schechter and Berger, 1967, *Biochem Biophys Res Commun* 27: 157-162, Schechter and Berger, 1968, *Biochem Biophys Res Commun* 32: 898-902). The residues in C-terminal direction are designated P1', P2', P3', P4'. The P positions are provided in the columns and the rows show amino acids in the different P positions. Positive values (Z-score) in the table reflect a preference for the amino acid residue in a certain P position in favor of trypsin ZT isoforms compared to trypsin I. Negative values (Z-score) reflect a preference in favor of trypsin I compared trypsin ZT. For example, based on the values from Table 3 it can be seen that trypsin ZT is much better adapted in cleaving peptides containing several consecutive positively charged residues (arginine or lysine) compared to trypsin I. Again, those types of sequences, that is lysine- and arginine-rich amino acid sequences, are frequently found in protein toxins, proteins and peptides involved in pathogenesis (Suzuki, Orba et al., 2010, *PLoS Pathog* 6: e1000801, Fentress, Steinfeldt et al., 2012, *Cell Microbiol* 14: 1921-1933, Jiang, Cun et al., 2012, *J Virol* 86: 7256-7267, Milletti, 2012, *Drug Discov Today* 17: 850-860, Gallaher and Garry, 2015, *Viruses* 7: 285-305). As previously mentioned, trypsin ZT isoforms have therefore properties beneficial against proteins responsible for the pathogenicity of many microorganisms.

TABLE 3

| | Amino acid | | | | | | | |
|---|---|---|---|---|---|---|---|---|
| | P4 | P3 | P2 | P1 | P1' | P2' | P3' | P4' |
| 5 min. Position | | | | | | | | |
| G | −0.60 | 0.88 | 0.48 | 0.26 | −1.21 | 0.11 | 0.97 | 0.08 |
| A | 0.01 | 0.48 | 1.92 | −0.57 | 2.31 | 1.01 | −0.62 | −0.14 |
| S | −0.06 | −0.04 | 0.43 | 0.23 | 0.25 | −0.52 | −1.47 | 0.32 |
| P | −1.04 | −0.59 | 0.39 | −0.16 | 0.25 | 1.86 | −0.30 | −0.50 |
| V | 0.99 | −1.14 | −1.88 | 0.23 | 0.43 | 0.54 | 0.01 | 0.38 |
| T | 0.05 | −1.40 | 0.43 | 0.72 | 0.48 | −0.02 | −1.39 | −0.06 |
| L | −0.50 | 0.48 | −2.26 | 0.25 | −0.75 | −0.43 | 0.88 | 0.91 |
| I | 1.42 | −0.51 | −0.31 | 0.72 | −0.67 | −0.36 | −0.04 | −0.62 |
| N | 0.95 | 0.93 | −0.47 | −0.15 | −1.33 | −0.79 | −0.56 | 0.02 |
| D | 0.33 | 0.43 | 0.24 | −0.48 | −0.02 | −0.53 | −0.52 | −0.69 |
| Q | −1.38 | −0.89 | −0.87 | 0.70 | −0.01 | −0.55 | −0.01 | 1.10 |
| K | −0.12 | 0.38 | 1.88 | −6.09 | 1.02 | −1.11 | −0.14 | −0.27 |
| E | 0.38 | −0.66 | −0.96 | 0.30 | −0.53 | −1.06 | 0.48 | −0.09 |
| M | −1.91 | −1.27 | −0.28 | 0.25 | −0.79 | −0.86 | 0.33 | 0.38 |
| H | −0.09 | 0.38 | 0.92 | 0.25 | −0.39 | 0.58 | 0.38 | 1.49 |
| F | 0.49 | −0.41 | −0.26 | 0.72 | −0.01 | −0.42 | −0.58 | 0.10 |
| R | −0.69 | −0.09 | −0.07 | 2.69 | 1.95 | 0.99 | 0.12 | 0.27 |
| Y | −0.60 | 0.75 | 1.04 | 0.23 | −0.15 | −0.42 | 0.95 | −0.12 |
| W | 1.00 | 0.64 | −0.84 | −0.15 | −0.59 | 1.00 | 1.36 | −0.53 |
| 15 min. Position | | | | | | | | |
| G | 0.33 | 1.65 | −0.27 | 0.48 | −0.64 | 0.60 | 1.79 | −0.36 |
| A | −0.34 | −0.66 | 1.33 | −0.52 | 1.88 | −0.60 | −1.05 | 0.17 |
| S | 0.30 | −0.41 | 0.73 | 0.44 | 0.51 | 0.03 | −1.16 | 0.55 |
| P | 0.26 | −0.62 | 0.23 | 0.12 | 0.54 | 1.70 | 0.66 | −0.79 |
| V | 0.55 | −0.08 | −0.75 | 0.44 | 0.36 | 0.97 | 0.97 | 0.81 |
| T | 0.04 | −0.25 | −0.50 | 0.89 | 0.44 | 0.81 | −1.21 | −0.63 |
| L | 0.49 | 0.11 | −1.57 | 0.18 | 0.18 | 0.44 | 0.73 | 0.73 |
| I | −1.07 | −0.89 | −0.97 | 0.44 | −0.54 | 0.12 | 0.32 | 0.04 |
| N | −0.86 | 0.81 | 0.96 | 0.89 | −1.50 | 0.67 | −1.74 | −0.89 |
| D | −1.45 | −0.43 | 0.07 | −0.03 | 0.11 | −2.02 | 0.42 | −0.76 |
| Q | −0.32 | −0.71 | −1.07 | 0.89 | −0.28 | −0.49 | 0.43 | 0.73 |
| K | −0.72 | −0.16 | 1.35 | −6.74 | 0.96 | −1.11 | 0.25 | 0.48 |
| E | 0.25 | −0.72 | −0.01 | 0.54 | −0.39 | −1.35 | −1.49 | 0.25 |
| M | −0.89 | −0.59 | −0.16 | 0.47 | 0.25 | −2.23 | 0.19 | 1.55 |
| H | 0.33 | 0.26 | 1.26 | 0.89 | −0.67 | 0.29 | −0.19 | 0.40 |
| F | 1.34 | 0.15 | −0.82 | 0.89 | −0.33 | −0.36 | −0.26 | 0.20 |
| R | −0.67 | −0.17 | −0.82 | −1.11 | 2.17 | 1.35 | 0.65 | −0.78 |
| Y | 0.30 | 0.40 | 0.58 | 0.44 | −1.00 | 0.57 | 0.89 | −1.07 |
| W | 0.49 | −0.26 | −1.38 | 0.13 | −1.83 | −0.57 | 0.36 | 0.50 |
| 60 min. Position | | | | | | | | |
| G | 0.45 | 0.80 | −1.05 | 0.26 | −0.27 | 0.71 | 0.65 | −0.93 |
| A | 0.05 | −0.74 | 1.65 | −0.30 | 2.33 | 0.39 | −0.43 | −1.56 |
| S | −0.30 | 0.57 | 0.52 | 0.52 | 0.60 | −1.19 | −0.08 | 0.59 |
| P | −0.72 | 0.42 | −1.24 | −0.05 | 0.90 | 2.28 | −0.28 | −0.57 |
| V | −0.25 | 0.51 | −0.09 | 0.84 | −0.55 | 1.03 | −0.19 | 0.91 |
| T | 0.49 | −0.07 | 0.91 | 0.52 | −0.54 | 0.80 | −1.21 | 0.13 |
| L | −0.23 | −0.47 | −0.73 | −0.06 | 0.66 | 0.22 | 0.41 | 0.38 |
| I | −0.73 | −0.53 | 0.04 | 0.20 | 0.44 | 0.20 | 0.85 | 0.61 |
| N | −0.90 | 0.15 | 0.28 | −0.05 | −1.49 | −0.43 | −1.18 | −0.18 |
| D | −1.33 | −0.03 | −0.16 | 1.32 | −0.70 | −1.42 | −0.26 | 0.67 |
| Q | 0.63 | −0.44 | −1.36 | 0.85 | 0.33 | −0.17 | −1.15 | 1.09 |
| K | 0.43 | −0.02 | 1.24 | −7.02 | 0.97 | −1.46 | 0.73 | 0.90 |
| E | −0.01 | −1.45 | −0.21 | 0.54 | −1.36 | −1.64 | −1.11 | −0.36 |
| M | −1.39 | −0.36 | 0.01 | 0.24 | −0.24 | −0.93 | −0.37 | 0.79 |
| H | 0.79 | −1.38 | 1.23 | 0.85 | −1.06 | −0.30 | 0.47 | 0.57 |
| F | 0.48 | 0.15 | −1.67 | 0.52 | −0.06 | 0.19 | 0.85 | −0.07 |
| R | −0.46 | −0.02 | −0.91 | −0.91 | 1.67 | 0.91 | 1.50 | −0.11 |
| Y | 0.73 | 0.41 | 0.25 | 0.52 | −1.36 | 0.58 | 1.60 | −2.25 |
| W | 0.85 | 1.02 | 0.09 | 0.90 | −0.21 | 0.03 | −0.49 | −0.42 |

Table 4 shows precursor ion intensities of selected peptides from multiplex profiling after incubation with trypsin ZT or with trypsin I. The precursor ion intensities are peptide peak intensities in the MS before fragmentation that represent a measure of relative abundance for a given species. X in peptide sequence denotes a placeholder for the absence of an amino acid in a peptide sequence. The data shows that trypsin ZT isoforms are exclusively able to cleave three peptide sequences (QGKKAPXX, WGNRSPLE and QAVRPNGM) compared to trypsin I. Furthermore, the data show that trypsin ZT isoforms preferentially cleave two peptides compared to trypsin I. Trypsin ZT isoforms were able to cleave XIARQPWN within 5 minutes and FDNRVGKW within 15 minutes whereas cleavage within these two peptides was only detected with trypsin I after 60 minute incubation.

TABLE 4

| Sequence | SEQ ID NO. | Ion Precursor Intensities | | | | | |
|---|---|---|---|---|---|---|---|
| | | Trypsin ZT | | | Trypsin I | | |
| | | 5' | 15' | 60' | 5' | 15' | 60' |
| QGKKAPXX | SEQ ID NO 14 | 175343 | 278749 | 256859 | 0 | 0 | 0 |
| WGNRSPLE | SEQ ID NO 15 | 21152 | 42866 | 47692 | 0 | 0 | 0 |
| QAVRPNGM | SEQ ID NO 16 | 0 | 12772 | 29668 | 0 | 0 | 0 |
| FDNRVGKW | SEQ ID NO 17 | 0 | 187219 | 937228 | 0 | 0 | 164917 |
| XIARQPWN | SEQ ID NO 18 | 130793 | 0 | 350390 | 0 | 0 | 188625 |

Example 4

Purification of Cod Trypsin ZT Isoforms from Concentrated Cod Viscera Extract

About 12 liters of ultrafiltered and diafiltered concentrate as obtained in Example 1 was applied to a continuous connected series of about 1 liter packed chromatography columns, the first containing a CM fast flow cation exchange resin (GE healthcare), the second one a p-aminobenzamidine affinity ligand coupled to a sepharose resin (GE healthcare) and the third one DEAE fast flow anion exchange resin (GE healthcare). The CM and p-aminobenzamidine columns were pre-equilibrated with about 10 column volumes of 25 mM Tris buffer of pH 7.8, containing 2.5 mM calcium chloride. The concentrate was pumped onto the CM and p-aminobenzamidine columns at a flow rate of about 100 ml per minute. When the application of the concentrated solution onto the columns was completed, residual material was washed off the continuous column system with about 8 liters of buffer A. After this wash was completed, the p-aminobenzamidine affinity column was disconnected from the CM column and washed with about 5 column volumes of a high salt solution of 25 mM Tris buffer pH 7.5 containing 0.5 M NaCl and 2.5 mM calcium chloride. The cod trypsins were then desorbed from the affinity ligand and eluted off the column with an acid solution of 25 mM acetic acid pH 3.2 containing 10 mM calcium chloride and 30% glycerol. The cod trypsin fraction was collected into a neutralizing buffer of 200 mM Tris pH 8.5 containing 30% glycerol. The DEAE anion exchange column was pre-equilibrated with about 10 column volumes of 25 mM Tris buffer of pH 7.8, containing 2.5 mM calcium chloride. The cod trypsin fraction was applied to the DEAE anion exchange resin and washed with about 5 column volumes of the equilibration buffer. Trypsin ZT isoforms were then desorbed from the column using up to a 0.9 M NaCl gradient salt solution. The purified cod trypsin ZT isoform preparation was homogeneous by SDS PAGE electrophoresis and FPLC Mono Q chromatography. The purified preparation was filter-sterilized through a 0.22 micron filter and stored frozen at about −20° C.

Example 5

Preparation of a Hydrogel Preparation of Cod Trypsins, Including Cod Trypsin ZT Isoforms The purified cod trypsin ZT isoform containing preparation of Example 2 was mixed with hydrocolloid gel comprising an aqueous gel containing 0.8% w/v Carbomer 940 and 40% glycerol. The cod trypsin preparation was mixed in a 1:1 ratio with the hydrogel to give a final concentration of 4 enzyme unit per mg (U/mg) of the final gel-enzyme mixture (the enzyme hydrogel ointment), the enzyme unit being determined using Cbz-GPR-pNA as substrate as previously described. Thus, the resulting enzyme hydrogel ointment contained about 0.01 mg/ml, or 1 U/ml of the cod trypsin enzymes, 0.4% Carbomer 940, 20% glycerol and 0.04% paraoxybenzoate.

Example 6

Antiviral Activity of Trypsin ZT Isoforms Against Enterovirus as a Model for Rhinovirus Picornaviruses are small single-stranded positive sense RNA viruses that lack a lipid envelope. Enterovirus and rhinovirus are two genera of Picornaviridae. Enterovirus replicates initially in the oropharynx and survives the acidic environment of the stomach. The small intestine is the major invasion site of enterovirus. Rhinovirus replicates in the nasal passages but is destroyed in the acidic environment of the stomach. Rhinovirus and enterovirus have an identical morphology but can be distinguished based on clinical, biophysical and epidemiological studies. Rhinovirus is problematic to handle in cell cultures (Racaniello, 2007, *Fields virology*, 5th ed: 795-838). Therefore, enterovirus was used as a model for rhinovirus to analyze the antiviral properties of trypsin ZT isoforms.

Materials and Methods

Enterovirus Stock Solution

Enterovirus (Coxsackievirus B2) was isolated from a patient at the University Hospital of Iceland, department of Virology and grown in MA-104 cells (African green monkey kidney cells) or Vero cells (African green monkey kidney cells). The Coxsackievirus B2 was titrated ($TCID_{50}$=8.23) according to Reed-Muench (REED and MUENCH, 1938, *American Journal of Epidemiology* 27: 493-497).

Enzyme Isoforms

Cod trypsin isoenzymes were separated by applying benzamidine purified cod trypsin to a MonoQ HR 5/5 ion exchange column. For isolation of trypsin ZT isoforms, the column was equilibrated with 25 mM Tris, 25 mM $CaCl_2$, pH 7.5, and the enzymes were eluted with a linear 0-400 mM NaCl gradient in 5 column volumes, linear 400-1000 mM NaCl in 20 column volumes at a flow rate of 1 mL/min.

Treatment

The MA-104 cells were grown in a 96-well microtiter plate to 95% confluency. The enterovirus was diluted from a stock solution to $10^{-6}$ using minimum essential medium (MEM) and 1.5 mL of the diluted solution was placed in two different vials. The vials were treated with 1.5 mL of trypsin ZT isoforms and 1.5 mL MEM as positive control. Negative control was MEM (3 mL) without virus. All vials were incubated at 34° C. and 5% $CO_2$ for 90 min before adding 100 μL of benzamidine agarose solution to remove residual trypsin and incubated for another 30 min. The solution was centrifuged at 5500 rpm for 3 min before placing 2 mL of the supernatant into an Eppendorf vial. 200 μL of the solution was placed in each well, total of 10 wells in the microtiter plate. The plate was incubated for 30 min. After incubation, the media was thrown off and MEM with 1% newborn calf serum (NCS) added to all the wells. A microscope was used to monitor for the presence of infection.

Results

Figure 5:
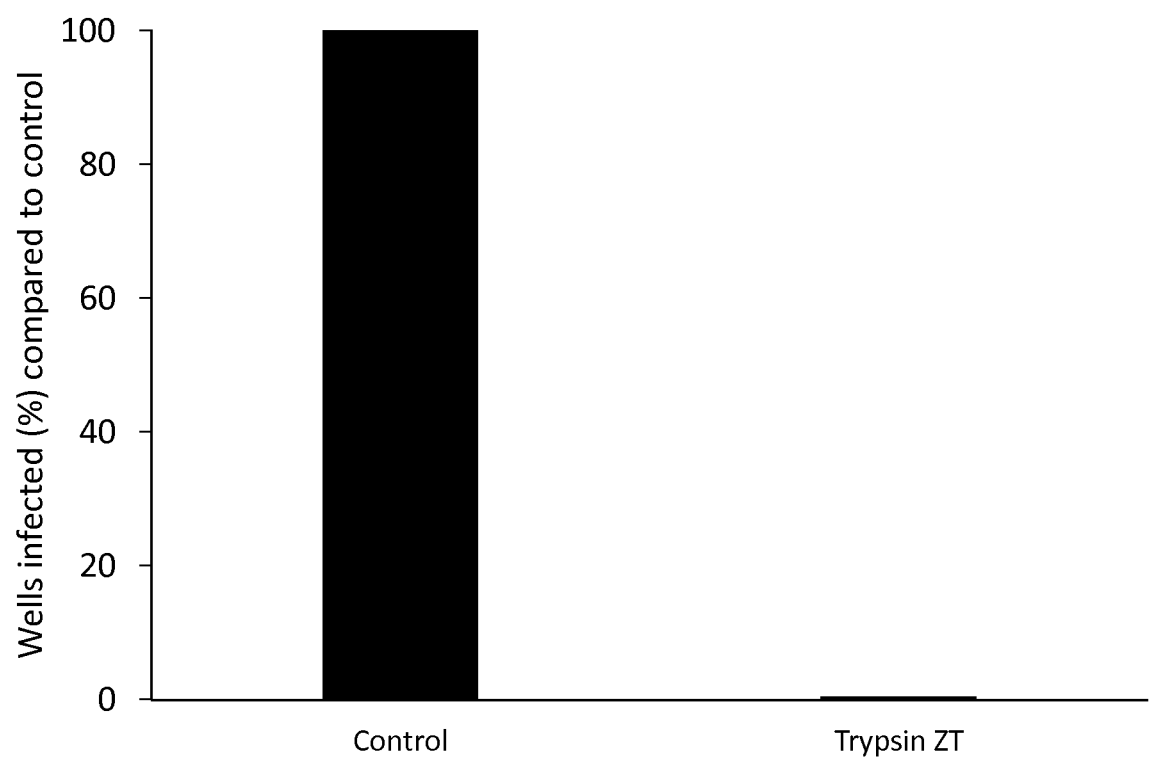
FIG. 5 shows antiviral activity of trypsin ZT against enterovirus (Coxsackievirus B2). The Y axis shows the percentage of wells infected compared to control and the X axis shows control (left bar) and treatment with trypsin ZT isoforms (right bar).

Trypsin ZT isoforms were very effective as antiviral agents against enterovirus (Coxsackievirus B2) that was used as a model for rhinovirus. The results are presented in FIG. 5.

---

The invention claimed is:

1. A composition comprising at least one isolated cod trypsin ZT isoform comprising an amino acid sequence according to SEQ ID NO:1 together with suitable excipients and carriers, wherein the composition:
   a) is in a medical device;
   b) comprises a polyvalent alcohol or polyol;
   c) is an ointment, gel, cream, lotion, hydrogel or suppository composition; or
   d) is formulated for oral administration in the form of a tablet, a capsule, a lozenge, a troche, a powder or chewing gum.

2. The composition according to claim 1, wherein the at least one isolated cod trypsin ZT isoform is elected from cod trypsin ZT-1 comprising an amino acid sequence according to SEQ ID NO:2; cod trypsin ZT-2 comprising an amino acid sequence according to SEQ ID NO:3; cod trypsin ZT-3 comprising an amino acid sequence according to SEQ ID NO:4; and cod trypsin ZT-4 comprising an amino acid sequence according to SEQ ID NO:5.

3. The composition according to claim 1, wherein the the hydrogel comprises a polyol.

4. The composition according to claim 3, wherein said cod trypsin ZT isoform(s) are present in admixture with other cod trypsins.

5. The composition according to claim 4, wherein said cod trypsin ZT isoform(s) comprises at least 5% w/w of the total content of cod trypsins in said composition.

6. The composition according to claim 1, wherein the medical device is a pressurized metered-dose inhaler.

7. The composition according to claim 1, wherein the polyvalent alcohol is a glycerol.

8. A method of removing dead or peeling skin from otherwise healthy skin comprising administering a composition according to claim 1 to the skin of a patient.

9. A method of improving the appearance of skin comprising administering a composition according to claim 1 to the skin of a patient.

10. The method according to claim 9, said composition further comprising an additional cosmetically active compound.

11. A method of treating disease, comprising administering a therapeutically effective amount of a composition according to claim 1, to a patient in need thereof wherein said disease is selected from pain, acute inflammation, chronic inflammation, arthritis, inflamed joints, bursitis, osteoarthritis, rheumatoid arthritis, juvenile rheumatoid arthritis, septic arthritis, fibromyalgia, systemic lupus erythematosus, phlebitis, tendinitis, rash, psoriasis, acne, eczema, facial seborrheic eczema, eczema of the hands, face or neck, foreskin infections, athlete's foot, fistulae infections, infected topical ulcers, navel infections in newborns, wrinkles, scars, kelloids, boils, warts and allergic itch, hemorrhoids, a fungal infection, an immunological disorder including an autoimmune disease, a wound infection or a wound from a burn.

12. The method according claim 11, wherein said disease is caused by a pathogenic organism selected from the group consisting of a virus, a bacterium, a fungus, a parasite and a protozoan.

13. A method of preparing a composition according to claim 1 comprising
    (i) preparing an aqueous extract of cod viscera,
    (ii) subjecting the aqueous extract to at least one or chromatography step, including an affinity chromatography step using a p-aminobenzamidine affinity ligand, and
    (iii) desorbing and eluting the at least one isolated cod trypsin ZT isoform comprising an amino acid sequence according to SEQ ID NO:1 bound to the p-aminobenzamidine affinity ligand.

14. The method according to claim 13, further comprising at least one step using an anionic exchange resin after said affinity chromatography step (ii).

15. The method according to claim 13, further comprising at least one step using a cation exchange resin prior to the affinity chromatography step (ii).

16. The method according to claim 13, wherein said desorbed and eluted cod trypsin ZT isoforms are sterile filtered using a filter with 0.45 µm or smaller pore size.

17. The method according to claim 13, wherein said cod trypsin ZT isoforms are selected from trypsin ZT-1, comprising an amino acid sequence according to SEQ ID NO:2; trypsin ZT-2 comprising an amino acid sequence according to SEQ ID NO:3; trypsin ZT-3 comprising an amino acid sequence according to SEQ ID NO:4; and trypsin ZT-4, comprising an amino acid sequence according to SEQ ID NO:5, or a mixture thereof.

18. A medical device comprising a composition according to claim 1.

19. The composition of claim 1, wherein the composition comprises a polyvalent alcohol and is formulated for topical administration or in a mouth or nasal spray.

* * * * *